US009931378B2

(12) United States Patent
Egan et al.

(10) Patent No.: US 9,931,378 B2
(45) Date of Patent: *Apr. 3, 2018

(54) METHOD OF IMMUNOTHERAPY FOR TREATMENT OF HUMAN PAPILLOMAVIRUS INFECTION

(71) Applicant: IRX Therapeutics, Inc., New York, NY (US)

(72) Inventors: James E. Egan, Stony Brook, NY (US); Martin Kast, La Canada, CA (US); Harvey Brandwein, East Hills, NY (US)

(73) Assignee: IRX Therapeutics, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/097,693

(22) Filed: Apr. 13, 2016

(65) Prior Publication Data

US 2016/0303198 A1 Oct. 20, 2016

Related U.S. Application Data

(63) Continuation of application No. 13/514,688, filed as application No. PCT/US2010/059450 on Dec. 8, 2010, now Pat. No. 9,333,238.

(60) Provisional application No. 61/267,590, filed on Dec. 8, 2009.

(51) Int. Cl.
| | |
|---|---|
| *A61K 38/19* | (2006.01) |
| *A61K 38/20* | (2006.01) |
| *A61K 38/21* | (2006.01) |
| *C07K 14/52* | (2006.01) |
| *C07K 14/54* | (2006.01) |
| *A61K 31/675* | (2006.01) |
| *A61K 45/06* | (2006.01) |
| *A61K 9/00* | (2006.01) |
| *A61K 31/405* | (2006.01) |
| *A61K 31/664* | (2006.01) |

(52) U.S. Cl.
CPC .......... *A61K 38/217* (2013.01); *A61K 9/0019* (2013.01); *A61K 31/405* (2013.01); *A61K 31/664* (2013.01); *A61K 31/675* (2013.01); *A61K 38/191* (2013.01); *A61K 38/193* (2013.01); *A61K 38/204* (2013.01); *A61K 38/2006* (2013.01); *A61K 38/208* (2013.01); *A61K 38/2013* (2013.01); *A61K 38/2046* (2013.01); *A61K 38/2053* (2013.01); *A61K 38/2086* (2013.01); *A61K 45/06* (2013.01); *A61K 2300/00* (2013.01)

(58) Field of Classification Search
CPC .......... A61K 2039/55522; A61K 38/19; A61K 38/20; A61K 38/2006; A61K 38/2013; A61K 38/217; C07K 14/52; C07K 14/54

See application file for complete search history.

(56) References Cited

U.S. PATENT DOCUMENTS

| | | | |
|---|---|---|---|
| 4,079,127 A | 3/1978 | Goldstein et al. |
| 4,116,951 A | 9/1978 | Wang |
| 4,148,788 A | 4/1979 | Wang |
| 4,293,455 A | 10/1981 | Merrifield et al. |
| 4,353,821 A | 10/1982 | Birr et al. |
| 4,390,623 A | 6/1983 | Frabricius et al. |
| 4,406,830 A | 9/1983 | Fabricius et al. |
| 4,448,879 A | 5/1984 | Fabricius et al. |
| 4,464,355 A | 8/1984 | Fabricius et al. |
| 4,466,918 A | 8/1984 | Birr et al. |
| 4,470,926 A | 9/1984 | Birr et al. |
| 4,504,415 A | 3/1985 | Felix et al. |
| 4,612,365 A | 9/1986 | Birr et al. |
| 4,614,731 A | 9/1986 | Horecker |
| 4,659,694 A | 4/1987 | Horecker |
| 4,716,148 A | 12/1987 | Horecker |
| 4,910,296 A | 3/1990 | Birr et al. |

(Continued)

FOREIGN PATENT DOCUMENTS

| | | |
|---|---|---|
| CN | 1106297 A | 8/1995 |
| EP | 0 041 189 A1 | 12/1981 |

(Continued)

OTHER PUBLICATIONS

International Search Report and Written Opinion dated Feb. 11, 2011 for Application No. PCT/US10/59450.
International Preliminary Report on Patentability dated Jun. 21, 2012 for Application No. PCT/US10/59450.
Albert et al., Dendritic cells acquire antigen from apoptotic cells and induce class I-restricted CTLs. Nature. Mar. 5, 1998;392(6671):86-9.
Almand et al., Clinical significance of defective dendritic cell differentiation in cancer. Clin Cancer Res. May 2000;6(5):1755-66.
Alvarez et al., Human T cell growth factor. I. Optimal conditions for its production. J Immunol. Sep. 1979;123(3):977-83.

(Continued)

*Primary Examiner* — Robert S Landsman
*Assistant Examiner* — Bruce D. Hissong
(74) *Attorney, Agent, or Firm* — Wolf, Greenfield & Sacks, P.C.

(57) ABSTRACT

A method of treating human papillomavirus (HPV), by administering a therapeutically effective amount of a primary cell-derived biologic to a patient infected with HPV, and inducing an immune response to HPV. A method of overcoming HPV-induced immune suppression of Langerhans cells (LC), by administering a therapeutically effective amount of a primary cell-derived biologic to a patient infected with HPV, and activating LC. A method of increasing LC migration towards lymph nodes, by administering a therapeutically effective amount of a primary cell-derived biologic to a patient infected with HPV, activating LC, and inducing LC migration towards lymph nodes. A method of generating immunity against HPV, by administering an effective amount of a primary cell derived biologic to a patient infected with HPV, generating immunity against HPV, and preventing new lesions from developing.

16 Claims, 9 Drawing Sheets

(56) References Cited

U.S. PATENT DOCUMENTS

| | | |
|---|---|---|
| 5,098,702 A | 3/1992 | Zimmerman et al. |
| 5,100,664 A | 3/1992 | Doyle et al. |
| 5,503,828 A | 4/1996 | Testa et al. |
| 5,503,841 A | 4/1996 | Doyle et al. |
| 5,632,983 A | 5/1997 | Hadden |
| 5,643,565 A | 7/1997 | Doyle et al. |
| 5,679,356 A | 10/1997 | Bonnem et al. |
| 5,698,194 A | 12/1997 | Hadden |
| 5,747,024 A | 5/1998 | Grabstein et al. |
| 5,788,963 A | 8/1998 | Murphy et al. |
| 5,800,810 A | 9/1998 | Doyle et al. |
| 5,849,307 A | 12/1998 | Metz et al. |
| 5,849,589 A | 12/1998 | Tedder et al. |
| 5,866,115 A | 2/1999 | Kanz et al. |
| 6,017,527 A | 1/2000 | Maraskovsky et al. |
| 6,060,068 A | 5/2000 | Doyle et al. |
| 6,274,378 B1 | 8/2001 | Steinman et al. |
| 6,350,589 B1 | 2/2002 | Morris et al. |
| 6,482,389 B1 | 11/2002 | Hadden |
| 6,759,239 B2 | 7/2004 | Suciu-Foca et al. |
| 6,896,879 B2 | 5/2005 | Talor |
| 6,977,072 B2 | 12/2005 | Hadden |
| 7,153,499 B2 | 12/2006 | Hadden |
| 7,182,942 B2 | 2/2007 | Hadden |
| 7,374,751 B1 | 5/2008 | Hancock |
| 7,731,945 B2 | 6/2010 | Hadden |
| 7,993,660 B2 | 8/2011 | Hadden et al. |
| 8,470,562 B2 | 6/2013 | Fennington, Jr. et al. |
| 8,591,956 B2 | 11/2013 | Hadden et al. |
| 8,784,796 B2 | 7/2014 | Hadden |
| 9,333,238 B2 | 5/2016 | Egan et al. |
| 2001/0053361 A1 | 12/2001 | Thompson et al. |
| 2002/0034494 A1 | 3/2002 | Vicari et al. |
| 2002/0058019 A1 | 5/2002 | Berenson et al. |
| 2002/0146397 A1 | 10/2002 | Hadden |
| 2002/0159953 A1 | 10/2002 | Hadden |
| 2003/0007955 A1 | 1/2003 | Rees et al. |
| 2003/0206885 A1 | 11/2003 | Hadden |
| 2004/0001829 A1 | 1/2004 | June et al. |
| 2004/0071658 A1 | 4/2004 | Hadden et al. |
| 2004/0136952 A1 | 7/2004 | Bhaskaran et al. |
| 2005/0008614 A1 | 1/2005 | Nieland et al. |
| 2005/0124645 A1 | 6/2005 | Finkel |
| 2005/0152874 A1 | 7/2005 | Hadden |
| 2006/0120996 A1 | 6/2006 | Hadden |
| 2006/0140983 A1 | 6/2006 | Palucka et al. |
| 2006/0194242 A1 | 8/2006 | Hadden |
| 2007/0025958 A1 | 2/2007 | Hadden |
| 2007/0031372 A1 | 2/2007 | Hadden |
| 2007/0041956 A1 | 2/2007 | Hadden |
| 2007/0065415 A1 | 3/2007 | Kleinsek et al. |
| 2007/0128174 A1 | 6/2007 | Kleinsek et al. |
| 2007/0154399 A1 | 7/2007 | Hadden |
| 2007/0196335 A1 | 8/2007 | Pardoll et al. |
| 2007/0259330 A1 | 11/2007 | Goddard et al. |
| 2008/0138365 A1 | 6/2008 | Berinstein et al. |
| 2008/0220000 A1 | 9/2008 | Moore et al. |
| 2009/0041797 A1 | 2/2009 | Davis et al. |
| 2009/0180982 A1 | 7/2009 | Hadden, Sr. |
| 2009/0181078 A1 | 7/2009 | Reed et al. |
| 2009/0258395 A1 | 10/2009 | Fennington, Jr. et al. |
| 2010/0047182 A1 | 2/2010 | Hadden |
| 2010/0047205 A1 | 2/2010 | Hadden et al. |
| 2010/0310469 A1 | 12/2010 | Hadden |
| 2011/0044941 A1 | 2/2011 | Hadden |
| 2011/0076249 A1 | 3/2011 | Hadden et al. |
| 2011/0081313 A1 | 4/2011 | Hadden |
| 2011/0110884 A1 | 5/2011 | Hadden et al. |
| 2012/0064035 A1 | 3/2012 | Hadden et al. |
| 2012/0141512 A1 | 6/2012 | Hadden et al. |
| 2012/0244117 A1 | 9/2012 | Egan et al. |
| 2013/0164255 A1 | 6/2013 | Hadden et al. |
| 2013/0243723 A1 | 9/2013 | Hadden et al. |
| 2014/0010779 A1 | 1/2014 | Hadden |
| 2014/0010780 A1 | 1/2014 | Hadden |
| 2014/0023593 A1 | 1/2014 | Hadden |
| 2014/0030217 A1 | 1/2014 | Hadden et al. |
| 2014/0348782 A1 | 11/2014 | Hadden |
| 2014/0348783 A1 | 11/2014 | Hadden |

FOREIGN PATENT DOCUMENTS

| | | |
|---|---|---|
| EP | 0 433 765 A1 | 6/1991 |
| EP | 0 974 357 A1 | 1/2000 |
| EP | 0 789 588 B1 | 1/2005 |
| EP | 0 787 008 B1 | 1/2009 |
| EP | 1 653 912 B1 | 10/2011 |
| EP | 1 998 811 B1 | 10/2012 |
| JP | 8-511166 A | 11/1996 |
| JP | 10-509955 | 9/1998 |
| JP | 11-504814 A | 5/1999 |
| JP | 2002-531521 A | 9/2002 |
| JP | 2008-502605 A | 1/2008 |
| JP | 2009-530308 A | 8/2009 |
| JP | 2009-197032 A | 9/2009 |
| WO | WO 87/06830 A1 | 11/1987 |
| WO | WO 89/09619 A1 | 10/1989 |
| WO | WO 94/13314 A1 | 6/1994 |
| WO | WO 95/04548 A1 | 2/1995 |
| WO | WO 96/15800 A1 | 5/1996 |
| WO | WO 96/15808 A1 | 5/1996 |
| WO | WO 96/34956 A1 | 11/1996 |
| WO | WO 97/31119 A1 | 8/1997 |
| WO | WO 99/20788 A1 | 4/1999 |
| WO | WO 99/40938 A2 | 8/1999 |
| WO | WO 00/06723 A1 | 2/2000 |
| WO | WO 00/33870 A2 | 6/2000 |
| WO | WO 01/24771 A1 | 4/2001 |
| WO | WO 02/034119 A2 | 5/2002 |
| WO | WO 03/035004 A2 | 5/2003 |
| WO | WO 03/061566 A2 | 7/2003 |
| WO | WO 2005/025494 A2 | 3/2005 |
| WO | WO 2005/120550 A2 | 12/2005 |
| WO | WO 2005/123120 A1 | 12/2005 |
| WO | WO 2007/067782 A2 | 6/2007 |
| WO | WO 2007/136910 A2 | 11/2007 |
| WO | WO 2008/014220 A2 | 1/2008 |
| WO | WO 2008/101154 A2 | 8/2008 |
| WO | WO 2008/133983 A1 | 11/2008 |
| WO | WO 2009/070639 A1 | 6/2009 |
| WO | WO 2009/137238 A2 | 11/2009 |
| WO | WO 2009/146392 A1 | 12/2009 |
| WO | WO 2010/132867 A1 | 11/2010 |
| WO | WO 2011/072006 A1 | 6/2011 |
| WO | WO 2012/037551 A2 | 3/2012 |

OTHER PUBLICATIONS

Bajénoff et al., Stromal cell networks regulate lymphocyte entry, migration, and territoriality in lymph nodes. Immunity. Dec. 1, 2006;25(6):989-1001.

Banchereau et al., Immunobiology of dendritic cells. Annu Rev Immunol. 2000;18:767-811.

Barrera et al., Clinical and pathological bio-responses induced with a cytokine mixture (IRX-2) in patients with oral cavity squamous cell carcinoma. Clinical and Applied Immunology Rev. 2001;1:181-5.

Barrera et al., Clinical and pathological responses induced by a neoadjuvant treatment with a cytokine mixture (IRX-2) in oral cavity squamous cell carcinoma of head and neck. Int J Immunorehab. 2000;2(3):29-32.

Barrera et al., Combination immunotherapy of squamous cell carcinoma of the head and neck: a phase 2 trial. Arch Otolaryngol Head Neck Surg. Mar. 2000;126(3):345-51.

Barrera et al., Neoadjuvant immunological treatment with IRX-2 in patients with advanced oral cavity squamous cell carinoma of the head and neck induces clinical and histological responses. First World Congress on Head and Neck Oncology. 1998:1017-20.

Barrera et al., Nursing care makes a difference. Application of the Omaha System. Outcomes Manag. Oct.-Dec. 2003;7(4):181-5.

Belldegrun et al., Adoptive immunotherapy of urologic tumors. Urologic Oncology. Cancer Treatment and Research. 1989;46:213-33.

(56) References Cited

OTHER PUBLICATIONS

Belldegrun et al., Human tumor infiltrating lymphocytes. Analysis of lymphokine mRNA expression and relevance to cancer immunotherapy. J Immunol. Jun. 15, 1989;142(12):4520-6.
Bellone et al., Cancer immunotherapy: synthetic and natural peptides in the balance. Immunol Today. Oct. 1999;20(10):457-62.
Bellone et al., Processing of engulfed apoptotic bodies yields T cell epitopes. J Immunol. Dec. 1, 1997;159(11):5391-9.
Bender et al., Improved methods for the generation of dendritic cells from nonproliferating progenitors in human blood. J Immunol Methods. Sep. 27, 1996;196(2):121-35.
Berd et al., Effect of low dose cyclophosphamide on the immune system of cancer patients: reduction of T-suppressor function without depletion of the CD8+ subset. Cancer Res. Jun. 15, 1987;47(12):3317-21.
Berd et al., Potentiation of human cell-mediated and humoral immunity by low-dose cyclophosphamide. Cancer Res. Nov. 1984;44(11):5439-43.
Berd, Low doses of chemotherapy to inhibit suppressor T cells. Immunity to Cancer II. 1989;288:449-58.
Beuth et al., Thymosin alpha(1) application augments immune response and down-regulates tumor weight and organ colonization in BALB/c-mice. Cancer Lett. Oct. 16, 2000;159(1):9-13.
Borden, Interferons: rationale for clinical trials in neoplastic disease. Ann Intern Med. Sep. 1979;91(3):472-9. Review.
Borysiewicz et al., A recombinant vaccinia virus encoding human papillomavirus types 16 and 18, E6 and E7 proteins as immunotherapy for cervical cancer. Lancet. Jun. 1, 1996;347(9014):1523-7.
Brandwein, IRX-2: a natural cytokine stimulant for cancer vaccines. Session V: Strategies for immunization. Cancer Immunol Immunotherapy. Mar. 2003;52:S17-18, 30.
Cavaillon, Pro- versus Anti-Inflammatory Cytokines: Myth or Reality. Cell Mol Biol. 2001;47(4):695-702.
Cella et al., Inflammatory stimuli induce accumulation of MHC class II complexes on dendritic cells. Nature. Aug. 21, 1997;388(6644):782-7.
Cella et al., Ligation of CD40 on dendritic cells triggers production of high levels of interleukin-12 and enhances T cell stimulatory capacity: T-T help via APC activation. J Exp Med. Aug. 1, 1996;184(2):747-52.
Chang et al., Overview of interleukin-2 as an immunotherapeutic agent. Semin Surg Oncol. 1989;5(6):385-90. Review.
Chaux et al., Inflammatory cells infiltrating human colorectal carcinomas express HLA class II but not B7-1 and B7-2 costimulatory molecules of the T-cell activation. Lab Invest. May 1996;74(5):975-83.
Chen et al., Serum and mucosal immune responses to an inactivated influenza virus vaccine induced by epidermal powder immunization. J Virol. Sep. 2001;75(17):7956-65.
Chilson et al., Mitogenic lectins bind to the antigen receptor on human lymphocytes. Eur J Immunol. Feb. 1989;19(2):389-96.
Chirigos et al., Immunotherapeutic agents: their role in cellular immunity and their therapeutic potential. Springer Semin Immunopathol.1985;8(4):327-46.
Cirelli et al., Interferons in human papillomavirus infections. Antiviral Res. Jul. 1994;24(2-3):191-204.
Clerici et al., An Occam's razor approach to the immunopathogenesis of HIV infection. AIDS. 1995;9 Suppl A:S33-40.
Cohen et al., Pronounced acute immunosuppression in vivo mediated by HIV Tat challenge. Proc Natl Acad Sci U S A. Sep. 14, 1999;96(19):10842-7.
Coles et al., Adjuvant effect of aluminium monostearate paraffin gels on antitoxin response. J Pharm Pharmacol. 1965;17:87S-91S.
Cortesina et al., Interleukin-2 injected around tumor-draining lymph nodes in head and neck cancer. Head Neck. Mar.-Apr. 1991;13(2):125-31.
Cortesina et al., Temporary regression of recurrent squamous cell carcinoma of the head and neck is achieved with a low but not with a high dose of recombinant interleukin 2 injected perilymphatically. Br J Cancer. Mar. 1994;69(3):572-6.
Cortesina et al., Treatment of recurrent squamous cell carcinoma of the head and neck with low doses of interleukin-2 injected perilymphatically. Cancer. Dec. 15, 1988;62(12):2482-5.
Cowens et al., Inhibition of the development of suppressor cells in culture by 4-hydroperoxycyclophosphamide. J Immunol. 1984;132:95-100.
Cozzolino et al., Characterization of cells from invaded lymph nodes in patients with solid tumors. Lymphokine requirement for tumor-specific lymphoproliferative response. J Exp Med. Aug. 1, 1987;166(2):303-18.
Cross et al., Administration of a prostaglandin synthetase inhibitor associated with an increased immune cell infiltrate in squamous cell carcinoma of the head and neck. Arch Otolaryngol Head Neck Surg. May 1992;118(5):526-8.
Czystowska et al., Mechanisms of T-cell protection from death by IRX-2: a new immunotherapeutic. Cancer Immunol Immunother. Apr. 2011;60(4):495-506. doi: 10.1007/s00262-010-0951-9. Epub Dec. 23, 2010.
Dallal et al., The dendritic cell and human cancer vaccines. Curr Opin Immunol. Oct. 2000;12(5):583-8.
De Stefani et al., Improved survival with perilymphatic interleukin 2 in patients with resectable squamous cell carcinoma of the oral cavity and oropharynx. Cancer. Jul. 1, 2002;95(1):90-7.
De Vries et al., Effective migration of antigen-pulsed dendritic cells to lymph nodes in melanoma patients is determined by their maturation state. Cancer Res. Jan. 1, 2003;63(1):12-7.
Deans et al., CD45R as a primary signal transducer stimulating IL-2 and IL-2R mRNA synthesis by CD3-4-8- thymocytes. J Immunol. Oct. 15, 1989;143(8):2425-30.
Deepe et al., Pharmacological modulation of suppressor cell activity in mice with disseminated histoplasmosis. Infect Immun. Jul. 1983;41(1):114-20.
Den Otter et al., Local therapy of cancer with free IL-2. Cancer Immunol Immunother. Jul. 2008;57(7):931-50. doi: 10.1007/s00262-008-0455-z.
Dubey et al., Costimulatory requirements of naive CD4+ T cells. ICAM-1 or B7-1 can costimulate naive CD4 T cell activation but both are required for optimum response. J Immunol. Jul. 1, 1995;155(1):45-57.
Dueñas-Gonzalez et al., A pilot study of perilymphatic leukocyte cytokine mixture (IRX-2) as neoadjuvant treatment for early stage cervical carcinoma. Int Immunopharmacol. Jun. 2002;2(7):1007-16.
Dunn et al., Dendritic cells and HNSCC: a potential treatment option? Oncology Reports. 2005;13:3-10.
Eby, Treatment of acute lymphocytic leukemia using zinc adjuvant with chemotherapy and radiation—a case history and hypothesis. Med Hypotheses. 2005;64(6):1124-6.
Egan et al., IRX-2, a novel in vivo immunotherapeutic, induces maturation and activation of human dendritic cells in vitro. J Immunother. Sep. 2007;30(6):624-33.
Ehrke, Immunomodulation in cancer therapeutics. Int Immunopharmacol. Aug. 2003;3(8):1105-19.
Fahey et al., Reversal of human papillomavirus-specific T cell immune suppression through TLR agonist treatment of Langerhans cells exposed to human papillomavirus type 16. J Immunol. Mar. 1, 2009;182(5):2919-28. doi: 10.4049/jimmunol.0803645.
Favalli et al., Modulation of natural killer activity by thymosin alpha 1 and interferon. Cancer Immunol Immunother. 1985;20(3):189-92.
Ferraro et al., Co-delivery of PSA and PSMA DNA vaccines with electroporation induces potent immune responses. Hum Vaccin. Jan.-Feb. 2011;7 Suppl:120-7. Epub Jan. 1, 2011.
Forni et al., Interleukin 2 activated tumor inhibition in vivo depends on the systemic involvement of host immunoreactivity. J Immunol. Jun. 1, 1987;138(11):4033-41.
Frillingos et al., Appearance of thymosin alpha 1 in supernatants of monocytes incubated with prothymosin alpha. Arch Biochem Biophys. Jul. 1992;296(1):256-63.
Gabrilovich et al., Decreased antigen presentation by dendritic cells in patients with breast cancer. Clin Cancer Res. Mar. 1997;3(3):483-90.

(56) References Cited

OTHER PUBLICATIONS

Gabrilovich et al., Dendritic cells in antitumor immune responses. I. Defective antigen presentation in tumor-bearing hosts. Cell Immunol. May 25, 1996;170(1):101-10.

Gabrilovich et al., Production of vascular endothelial growth factor by human tumors inhibits the functional maturation of dendritic cells. Nat Med. Oct. 1996;2(10):1096-103.

Gabrilovich et al., Vascular endothelial growth factor inhibits the development of dendritic cells and dramatically affects the differentiation of multiple hematopoietic lineages in vivo. Blood. Dec. 1, 1998;92(11):4150-66.

Gallo et al., Cyclooxygenase-2 pathway correlates with VEGF expression in head and neck cancer. Implications for tumor angiogenesis and metastasis. Neoplasia. Jan.-Feb. 2001;3(1):53-61.

Galon et al., Type, density, and location of immune cells within human colorectal tumors predict clinical outcome. Science. Sep. 29, 2006;313(5795):1960-4.

Garaci et al., Thymosin alpha 1 in the treatment of cancer: from basic research to clinical application. Int J Immunopharmacol. Dec. 2000;22(12):1067-76. Review.

Garaci, Thymosin alpha1: a historical overview. Ann N Y Acad Sci. Sep. 2007;1112:14-20. Epub Jun. 13, 2007.

Gearing et al., Production and assay of the interleukins. J Immunol Methods. Oct. 24, 1985;83(1):1-27.

Gillis et al., T cell growth factor: parameters of production and a quantitative microassay for activity. J Immunol. Jun. 1978;120(6):2027-32.

Goldstein et al., The role of interferon in cancer therapy: a current perspective. CA Cancer J Clin. Sep.-Oct. 1988;38(5):258-77.

Goldstein et al., Thymosin alpha1: isolation and sequence analysis of an immunologically active thymic polypeptide. Proc Natl Acad Sci U S A. Feb. 1977;74(2):725-9.

Goldstein, Thymosin α1: chemistry, mechanism of action and clinical applications. Combination Therapies. Plenum Press. 1993;2:39-48.

Gollapudi et al, Effect of ciprofloxacin on mitogen-stimulated lymphocyte proliferation. Antimicrob Agents Chemother. Feb. 1986;29(2):337-8.

Hadden et al., A trial of IRX-2 in patients with squamous cell carcinomas of the head and neck. Int Immunopharmacol. Aug. 2003;3(8):1073-81.

Hadden et al., Immunopharmacologic bases of immunotherapy. Clin Physiol Biochem. 1985;3(2-3):111-9. Review.

Hadden et al., Immunopharmacology. Immunomodulation and immunotherapy. JAMA. Nov. 25, 1992;268(20):2964-9.

Hadden et al., Immunotherapy with natural interleukins and/or thymosin alpha 1 potently augments T-lymphocyte responses of hydrocortisone-treated aged mice. Int J Immunopharmacol. Oct. 1995;17(10):821-8.

Hadden et al., Interleukins and contrasuppression induce immune regression of head and neck cancer. Arch Otolaryngol Head Neck Surg. Apr. 1994;120(4):395-403.

Hadden et al., IRX-2 and thymosin alphal (Zadaxin) increase T lymphocytes in T lymphocytopenic mice and humans. Ann N Y Acad Sci. Sep. 2007;1112:245-55. Epub Jun. 28, 2007.

Hadden et al., Lymphocyte blast transformation. I. Demonstration of adrenergic receptors in human peripheral lymphocytes. Cell Immunol. Dec. 1970;1(6):583-95.

Hadden et al., Mixed interleukins and thymosin fraction V synergistically induce T lymphocyte development in hydrocortisone-treated aged mice. Cell Immunol. Oct. 1, 1992;144(1):228-36.

Hadden et al., Strategies of immune reconstitution: effects of lymphokines on murine T cell development in vitro and in vivo. Life Sci. 1989;44(13):v-xii.

Hadden et al., The characterization of immunotherapeutic agents. Immunopharmacol Reviews. Plenum Press. New York. 1990;1:1-64.

Hadden, Aspects of the immunopharmacology of thymosin alpha-1. Clinical Applied Reviews. Mar. 2001;1(3-4):187-91.

Hadden, Combination immunotherapy. Intl Immunopharm. 2003;3:1049-50.

Hadden, Immunodeficiency and cancer: prospects for correction. Int Immunopharmacol. Aug. 2003;3(8):1061-71.

Hadden, Immunology of Head and Neck Cancer. Contemporary Issues in Oral Cancer. New York. Oxford University Press. 2000:72-95.

Hadden, Immunology of head and neck cancer: prospects for immunotherapy. Clin Immunotherapy. 1995;3:362-85.

Hadden, Immunopharmacology. Immunomodulation and immunotherapy. JAMA. Nov. 27, 1987;258(20):3005-10.

Hadden, Immunostimulants. Immunol Today. Jun. 1993;14(6):275-80. Review.

Hadden, Immunotherapy of human immunodeficiency virus infection. TIPS review. 1991;12:107-11.

Hadden, T-cell adjuvants. Int J Immunopharmacol. Sep. 1994;16(9):703-10.

Hadden, The immunology and immunotherapy of breast cancer: an update. Int J Immunopharmacol. Feb. 1999;21(2):79-101.

Hadden, The immunopharmacology of head and neck cancer: an update. Int J Immunopharmacol. Nov.-Dec. 1997;19(11-12):629-44.

Hadden, The treatment of zinc deficiency is an immunotherapy. Int J Immunopharmacol. Sep. 1995;17(9):697-701.

Hadden, Thymic endocrinology. Ann N Y Acad Sci. May 1, 1998;840:352-8.

Hadden, Thymic endocrinology. Int J Immunopharmacol. Apr. 1992;14(3):345-52. Review.

Hank et al., Monoclonal antibodies, cytokines and fusion proteins in the treatment of malignant disease. Cancer Chemother Biol Response Modif. 1999;18:210-22.

Hart, Dendritic cells: unique leukocyte populations which control the primary immune response. Blood. Nov. 1, 1997;90(9):3245-87.

Heath et al., Cytokines as immunological adjuvants. Vaccine. 1992;10(7):427-34. Review.

Hengst et al., Cooperation between cyclophosphamide tumoricidal activity and host antitumor immunity in the cure of mice bearing large MOPC-315 tumors. Cancer Res. Jun. 1981;41(6):2163-7.

Hengst et al., Importance of timing in cyclophosphamide therapy of MOPC-315 tumor-bearing mice. Cancer Res. Jul. 1980;40(7):2135-41.

Hillman et al., Systemic treatment with interleukin-4 induces regression of pulmonary metastases in a murine renal cell carcinoma model. Cell Immunol. Feb. 1995;160(2):257-63.

Hirsch et al., Immunostimulation of patients with head and neck cancer. In vitro and preliminary clinical experiences. Arch Otolaryngol. May 1983;109(5):298-301.

Hodge et al., A triad of costimulatory molecules synergize to amplify T-cell activation. Cancer Res. Nov. 15, 1999;59(22):5800-7.

Hoffmann et al., Alterations in the frequency of dendritic cell subsets in the peripheral circulation of patients with squamous cell carcinomas of the head and neck. Clin Cancer Res. Jun. 2002;8(6):1787-93.

Holtl et al., Immunotherapy of metastatic renal cell carcinoma with tumor lysate-pulsed autologous dendritic cells. Clin Cancer Res. Nov. 2002;8(11):3369-76.

Hwu et al., The genetic modification of T cells for cancer therapy: an overview of laboratory and clinical trials. Cancer Detect Prev. 1994;18(1):43-50. Review.

Hwu et al., The use of gene-modified tumor-infiltrating lymphocytes for cancer therapy Ann N Y Acad Sci. May 31, 1994;716:188-97; discussion 197-203.Review.

Johnston-Early et al., Delayed hypersensitivity skin testing as a prognostic indicator in patients with small cell lung cancer. Cancer. Oct. 15, 1983;52(8):1395-400.

Jordan et al., Optimal analysis of composite cytokine responses during alloreactivity. J Immunol Methods. Feb. 1, 2002;260(1-2):1-14.

June et al., Evidence for the involvement of three distinct signals in the induction of IL-2 gene expression in human T lymphocytes. J Immunol. Jul. 1, 1989;143(1):153-61.

(56) References Cited

OTHER PUBLICATIONS

Kaech et al., Effector and memory T-cell differentiation: implications for vaccine development. Nat Rev Immunol. Apr. 2002;2(4):251-62.
Kalinski et al., Prostaglandin E(2) is a selective inducer of interleukin-12 p40 (IL-12p40) production and an inhibitor of bioactive IL-12p70 heterodimer. Blood. Jun. 1, 2001;97(11):3466-9.
Kameda et al., Mixed lymphokines in low dose prolong life in cyclophosphamide-treated melanoma-bearing mice. Int J Immunother. 1992;8:1-5.
Kaminuma et al., Interleukin-5 production by peripheral blood mononuclear cells of asthmatic patients is suppressed by T-440: relation to phosphodiesterase inhibition. J Pharmacol Exp Ther. Oct. 1996;279(1):240-6.
Katsuyuki et al., Clinical trials of immunotherapy for advanced prostate cancer. Urologic Oncology. 2000;5:265-73.
Kavanaugh et al., Immunologic dysfunction in cancer. Hematol Oncol Clin North Am. Aug. 1996;10(4):927-51.
Kidd, Th1/Th2 balance: the hypothesis, its limitations, and implications for health and disease. Altern Med Rev. Aug. 2003;8(3):223-46.
Kleindienst et al., Endogenous dendritic cells are required for amplification of T cell responses induced by dendritic cell vaccines in vivo. J Immunol. Mar. 15, 2003;170(6):2817-23.
Koopman et al., Reversal of human papillomavirus immune escape using IRX-2 and a toll-like receptor 3 agonist. Online. Available at http://scripties.umcg.eldoc.ub.rug.nl/root/geneeskunde/2010/KoopmanMaaike/. Jan. 1, 2011. Retrieved from the Internet on Jan. 22, 2011. Abstract only.
Kovacs et al., Increases in CD4 T lymphocytes with intermittent courses of interleukin-2 in patients with human immunodeficiency virus infection. A preliminary study. N Engl J Med. Mar. 2, 1995;332(9):567-75.
Lafferty et al., Immunological induction of T lymphocytes: role of antigen and the lymphocyte costimulator. Blood Cells 1978;4(3):395-406.
Lahiri et al., Engagement of TLR signaling as adjuvant: towards smarter vaccine and beyond. Vaccine. Dec. 9, 2008;26(52):6777-83.
Langenkamp et al., Kinetics of dendritic cell activation: impact on priming of TH1, TH2 and nonpolarized T cells. Nat Immunol. Oct. 2000;1(4):311-6.
Lanzavecchia et al., Understanding the generation and function of memory T cell subsets. Curr Opin Immunol. Jun. 2005;17(3):326-32.
Lopez et al., Biochemotherapy with thymosin alpha 1, interleukin-2 and dacarbazine in patients with metastatic melanoma: clinical and immunological effects. Ann Oncol. Oct. 1994;5(8):741-6.
López-Rodríguez et al., Interleukin-2 killer cells: in vitro evaluation of combination with prothymosin alpha. Lymphokine Cytokine Res. Jun. 1994;13(3):175-82.
Lou et al., Dendritic cells strongly boost the antitumor activity of adoptively transferred T cells in vivo. Cancer Res. Sep. 15, 2004;64(18):6783-90.
Maass et al., Priming of tumor-specific T cells in the draining lymph nodes after immunization with interleukin 2-secreting tumor cells: three consecutive stages may be required for successful tumor vaccination. Proc Natl Acad Sci U S A. Jun. 6, 1995;92(12):5540-4.
Mackall et al., Age, thymopoiesis, and CD4+ T-lymphocyte regeneration after intensive chemotherapy. N Engl J Med. Jan. 19, 1995;332(3):143-9.
Mackall, T-cell immunodeficiency following cytotoxic antineoplastic therapy: a review. Stem Cells. 2000;18(1):10-8.
MacLean et al., Enhancing the effect of THERATOPE STn-KLH cancer vaccine in patients with metastatic breast cancer by pretreatment with low-dose intravenous cyclophosphamide. J Immunother Emphasis Tumor Immunol. Jul. 1996;19(4):309-16.
Mantovani et al., Macrophage polarization: tumor-associated macrophages as a paradigm for polarized M2 mononuclear phagocytes. Trends Immunol. Nov. 2002;23 (11):549-55. Review.
Maric et al., Immunostimulatory activity of prothymosin-alpha in senescence. Ann N Y Acad Sci. 1991;621:148-58.
Maric et al., In vivo effect of prothymosin-alpha 1 on humoral and cell-mediated immune responses in the young rat. Int J Neurosci.Jul. 1991;59(1-3):135-42.
Marschner et al., CpG ODN enhance antigen-specific NKT cell activation via plasmacytoid dendritic cells. Eur J Immunol. Aug. 2005;35(8):2347-57.
Masek et al., Neuroendocrine immune interactions in health and disease. Int Immunopharmacol. Aug. 2003;3(8):1235-46.
Mastino et al., Combination therapy with thymosin alpha 1 potentiates the anti-tumor activity of interleukin-2 with cyclophosphamide in the treatment of the Lewis lung carcinoma in mice. Int J Cancer. Feb. 1, 1992;50(3):493-9.
Mastino et al., Thymosin alpha 1 potentiates interleukin 2-induced cytotoxic activity in mice. Cell Immunol. Mar. 1991;133(1):196-205.
Mastrangelo et al., Active specific immunization in the treatment of patients with melanoma. Semin Oncol. Dec. 1996;23(6):773-81.
Mattijssen et al., Clinical and immunopathological results of a phase II study of perilymphatically injected recombinant interleukin-2 in locally far advanced, nonpretreated head and neck squamous cell carcinoma. J Immunother (1991). Feb. 1991;10(1):63-8.
McLaughlin et al., Improved immunotherapy of a recombinant carcinoembryonic antigen vaccinia vaccine when given in combination with interleukin-2. Cancer Res. May 15, 1996;56(10):2361-7.
Mempel et al., Rulers over randomness: stroma cells guide lymphocyte migration in lymph nodes. Immunity. Dec. 2006;25(6):867-9.
Meneses et al., Histologic findings in patients with head and neck squamous cell carcinoma receiving perilymphatic natural cytokine mixture (IRX-2) prior to surgery. Arch Pathol Lab Med. May 1998;122(5):447-54.
Meneses et al., Lymph node histology in head and neck cancer: impact of immunotherapy with IRX-2. Int Immunopharmacol. Aug. 2003;3(8):1083-91.
Middel et al., Sinus histiocytosis with massive lymphadenopathy: evidence for its relationship to macrophages and for a cytokine-related disorder. Histopathology. Dec. 1999;35(6):525-33.
Mikysková et al., Local cytokine treatment of HPV16-associated tumors results in inhibition of their lung metastases. Clin Exp Metastasis. 2001;18(7):581-7.
Mitchell et al., Promotion of human T lymphocyte proliferation by IL-4. J Immunol. Mar. 1, 1989;142(5):1548-57.
Mohamadzadeh et al., Interleukin 15 Skews Monocyte Differentiation into Dendritic Cells with Features of Langerhans Cells. J Exp Med. 2001;194(7):1013-9.
Mokyr et al., Role of antitumor immunity in cyclophosphamide-induced rejection of subcutaneous nonpalpable MOPC-315 tumors. Cancer Res. Mar. 1982;42(3):974-9.
Moody et al., Thymosin alpha 1 down-regulates the growth of human non-small cell lung cancer cells in vitro and in vivo. Cancer Res. Nov. 1, 1993;53(21):5214-8.
Morgan et al., Selective in vitro growth of T lymphocytes from normal human bone marrows. Science. Sep. 10, 1976;193(4257):1007-8.
Mule, Mechanistic aspects of successful immunotherapy of established pulmonary metastases by the systemic administration of high-dose recombinant interleukin-2. Prog Clin Biol Res. 1987;244:79-91.
Murphy et al., Infusion of dendritic cells pulsed with HLA-A2-specific prostate-specific membrane antigen peptides: a phase II prostate cancer vaccine trial involving patients with hormone-refractory metastatic disease. Prostate. Jan. 1, 1999;38(1):73-8.
Musiani et al., Effect of low doses of interleukin-2 injected perilymphatically and periturmorally in patients with advanced primary head and neck squamous cell carcinoma. J Biol Response Mod. Dec. 1989;8(6):571-8.
Naylor et al., Preclinical and clinical studies on immunogenicity and safety of the HIV-1 p17-based synthetic peptide AIDS vaccine—HGP-30-KLH. Int J Immunopharmacol. 1991;13 Suppl 1:117-27.

(56) References Cited

OTHER PUBLICATIONS

Naylor et al., Enhancement of Peptide Specific DTH with Combination Cytokines. Presented CSHL Meeting Dec. 4-7, 2003. Molecular Approaches to Vaccine Design. p. 28.
Naylor et al., Immunopharmacology of thymosin alpha1 and cytokine synergy. Ann N Y Acad Sci. Sep. 2007;1112:235-44. Epub Jun. 13, 2007.
Naylor et al., IRX-2 increases the T cell-specific immune response to protein/peptide vaccines. Vaccine. Oct. 8, 2010;28(43):7054-62. Epub Aug. 13, 2010.
Naylor et al., Preclinical studies with an IRX-2 enhanced prostate vaccine. J Urology. 2008;179(4):45.
Naylor et al., Preclinical studies with IRX-2 and thymosin alpha1 in combination therapy. Ann N Y Acad Sci. Apr. 2010;1194:162-8.
Naylor et al., T cell targeted immune enhancement yields effective T cell adjuvants. Int Immunopharmacol. Aug. 2003;3(8):1205-15.
Nohria et al., Cytokines as potential vaccine adjuvants. Biotherapy. 1994;7(3-4):261-9.
O'Hagan et al., Recent developments in adjuvants for vaccines against infectious diseases. Biomol Eng. Oct. 15, 2001;18(3):69-85.
Overwijk et al., Creating therapeutic cancer vaccines: notes from the battlefield. Trends Immunol. Jan. 2001;22(1):5-7.
Paetkeau et al., Proliferation of murine thymic lymphocytes in vitro is mediated by the concanavalin A-induced release of a lymphokine (costimulator). J Immunol. Oct. 1976;117(4):1320-4.
Panje, Regression of head and neck carcinoma with a prostaglandin-synthesis inhibitor. Arch Otolaryngol. Nov. 1981;107(11):658-63.
Pulley et al., Intravenous, intralesional and endolymphatic administration of lymphokines in human cancer. Lymphokine Res. 1986;5 Suppl 1:S157-63.
Qin et al., Isolation and identification of a new thymic peptide from calf thymus. Biochem (Mosc). Aug. 2004;69(8):921-5.
Randolph et al., Is maturation required for Langerhans cell migration? J Exp Med. Aug. 19, 2002;196(4):413-6.
Randolph, Dendritic cell migration to lymph nodes: cytokines, chemokines, and lipid mediators. Semin Immunol. Oct. 2001;13(5):267-74.
Rapidis et al., Immunotherapy of head and neck cancer: current and future considerations. J Oncol. 2009;2009:346345. doi: 10.1155/2009/346345. Epub Aug. 9, 2009. 11 pages.
Rasi et al., Anti-tumor effect of combined treatment with thymosin alpha 1 and interleukin-2 after 5-fluorouracil in liver metastases from colorectal cancer in rats. Int J Cancer. Jun. 1, 1994;57(5):701-5.
Rasi et al., Combined treatment with thymosin-alpha1 and low dose interferon-alpha after dacarbazine in advanced melanoma. Melanoma Res. Apr. 2000;10(2):189-92.
Ridgway, The first 1000 dendritic cell vaccinees. Cancer Invest. 2003;21(6):873-86.
Riesbeck et al., Limited effects of temafloxacin compared with ciprofloxacin on T-lymphocyte function. Antimicrob Agents Chemother. Apr. 1994;38(4):879-82.
Riesenbeck et al., Superinduction of cytokine gene transcription by ciprofloxacin. J Immunol. Jul. 1, 1994;153(1):343-52.
Rogers et al., CD28, Ox-40, LFA-1, and CD4 modulation of Th1/Th2 differentiation is directly dependent on the dose of antigen. J Immunol. Mar. 15, 2000;164(6):2955-63.
Romani et al., Generation of mature dendritic cells from human blood. An improved method with special regard to clinical applicability. J Immunol Methods. Sep. 27, 1996;196(2):137-51.
Rosenberg et al., A progress report on the treatment of 157 patients with advanced cancer using lymphokine-activated killer cells and interleukin-2 or high-dose interleukin-2 alone. N Engl J Med. Apr. 9, 1987;316(15):889-97.
Rosenberg et al., Cancer immunotherapy: moving beyond current vaccines. Nat Med. Sep. 2004;10(9):909-15.
Rosenberg et al., Observations on the systemic administration of autologous lymphokine-activated killer cells and recombinant interleukin-2 to patients with metastatic cancer. N Engl J Med. Dec. 5, 1985;313(23):1485-92.
Rosenberg, Immunotherapy of cancer by systemic administration of lymphoid cells plus interleukin-2. J Biol Response Mod. Oct. 1984;3(5):501-11.
Rosenberg, The development of new immunotherapies for the treatment of cancer using interleukin-2. A review. Ann Surg. Aug. 1988;208(2):121-35. Review.
Saha et al., Zinc induces thymulin secretion from human thymic epithelial cells in vitro and augments splenocyte and thymocyte responses in vivo. Int J Immunopharmacol. Sep. 1995;17(9):729-33.
Saito et al., Spontaneous ex vivo apoptosis of peripheral blood mononuclear cells in patients with head and neck cancer. Clin Cancer Res. Jun. 1999;5(6):1263-73.
Sallusto et al., Dendritic cells use macropinocytosis and the mannose receptor to concentrate macromolecules in the major histocompatibility complex class II compartment: downregulation by cytokines and bacterial products. J Exp Med. Aug. 1, 1995;182(2):389-400.
Sallusto et al., Efficient presentation of soluble antigen by cultured human dendritic cells is maintained by granulocyte/macrophage colony-stimulating factor plus interleukin 4 and downregulated by tumor necrosis factor alpha. J Exp Med. Apr. 1, 1994;179(4):1109-18.
Sano et al., CpG Oligodeoxynucleotides as a Future Vaccine for Allergic Diseases. Allergol Intl. 2005;54:17-23.
Sasagawa, The Present Status and Significance in Implementation of Prophylactic Human Papillomavirus Vaccine in Japan. Modern Media. Oct. 2009;55(10):269-75. 17 pages.
Schuler-Thurner et al., Rapid induction of tumor-specific type 1 T helper cells in metastatic melanoma patients by vaccination with mature, cryopreserved, peptide-loaded monocyte-derived dendritic cells. J Exp Med. May 20, 2002;195(10):1279-88.
Schuloff, Thymic peptide hormones: basic properties and clinical applications in cancer. Crit Rev Oncol Hematol. 1985;3(4):309-76. Review.
Scott et al., Cell-mediated immune response to human papillomavirus infection. Clin Diagn Lab Immunol. Mar. 2001;8(2):209-20.
Scott et al., Th1 Cytokine Patterns in Cervical Human Papillomavirus Infection. Clin Diagn Lab Immunol. Sep. 1999; 6(5):751-5.
Sikorski et al., Dynamics of cervical langerhans cell counts in the course of HPV-positive CIN treatment with the use of human recombinant interferon gamma. Eur J Gynaecol Oncol. 2005;26(3):294-8.
Silecchia et al., Efficacy of repeated cycles of chemo-immunotherapy with thymosin alpha1 and interleukin-2 after intraperitoneal 5-fluorouracil delivery. Cancer Immunol Immunother. Jul. 1999:48(4):172-8.
Simmons et al., GM-CSF as a systemic adjuvant in a phase II prostate cancer vaccine trial. Prostate. Jun. 1, 1999;39(4):291-7.
Sozzani et al., Differential regulation of chemokine receptors during dendritic cell maturation: a model for their trafficking properties. J Immunol. Aug. 1, 1998;161(3):1083-6.
Steinman et al., Avoiding horror autotoxicus: the importance of dendritic cells in peripheral T cell tolerance. Proc Natl Acad Sci U S A. Jan. 8, 2002;99(1):351-8. Epub Jan. 2, 2002.
Steinman, The dendritic cell system and its role in immunogenicity. Annu Rev Immunol. 1991;9:271-96.
Syrjänen, Human papillomavirus (HPV) in head and neck cancer. J Clin Virol. Mar. 2005;32 Suppl 1:S59-66.
Tagawa, Cytokine therapy for cancer. Curr Pharm Des. Apr. 2000;6(6):681-99.
Talmage et al., Activation of cytotoxic T cells by nonstimulating tumor cells and spleen cell factor(s). Proc Natl Acad Sci U S A. Oct. 1977;74(10):4610-4.
Tas et al., Depressed monocyte polarization and clustering of dendritic cells in patients with head and neck cancer: in vitro restoration of this immunosuppression by thymic hormones. Cancer Immunol Immunother. 1993;36(2):108-14.
Thurman et al., Comparative evaluation of multiple lymphoid and recombinant human interleukin-2 preparations. J Biol Response Mod. Feb. 1986;5(1):85-107.

(56) References Cited

OTHER PUBLICATIONS

Tjoa et al., Development of dendritic-cell based prostate cancer vaccine. Immunol Lett. Sep. 15, 2000;74(1):87-93.

Tjoa et al., Evaluation of phase I/II clinical trials in prostate cancer with dendritic cells and PSMA peptides. Prostate. Jun. 15, 1998;36(1):39-44.

Tzehoval et al., Thymosins alpha 1 and beta 4 potentiate the antigen-presenting capacity of macrophages. Immunopharmacology. Sep.-Oct. 1989;18(2):107-13.

Valente et al., Infiltrating leukocyte populations and T-lymphocyte subsets in head and neck squamous cell carcinomas from patients receiving perilymphatic injections of recombinant interleukin 2. A pathologic and immunophenotypic study. Mod Pathol. Nov. 1990;3(6):702-8.

Van Den Eynde et al., T cell defined tumor antigens. Curr Opin Immunol. Oct. 1997;9(5):684-93.

Van Lier et al., Immobilized anti-CD3 monoclonal antibodies induce accessory cell-independent lymphokine production, proliferation and helper activity in human T lymphocytes. Immunology. Sep. 1989;68(1):45-50.

Verastegui et al. Immunological approach in the evaluation of regional lymph nodes of patients with squamous cell carcinoma of the head and neck. Clin Immunol. Jan. 2002;102(1):37-47.

Verastegui et al., A natural cytokine mixture (IRX-2) and interference with immune suppression induce immune mobilization and regression of head and neck cancer. Int J Immunopharmacol. Nov.-Dec. 1997;19(11-12):619-27.

Verastegui et al., Long-term immune dysfunction after radiotherapy to the head and neck area. Int Immunopharmacol. Aug. 2003;3(8):1093-1104.

Verwilghen et al., Differences in the stimulating capacity of immobilized anti-CD3 monoclonal antibodies: variable dependence on interleukin-1 as a helper signal for T-cell activation. Immunology. Feb. 1991;72(2):269-76.

Vine et al., T4 cell activation by immobilized phytohemagglutinin: differential capacity to induce IL-2 responsiveness and IL-2 production. J Immunol. Oct. 15, 1988;141(8):2593-600.

Waldmann et al., The multifaceted regulation of interleukin-15 expression and the role of this cytokine in NK cell differentiation and host response to intracellular pathogens. Annu Rev Immunol. 1999;17:19-49. Review.

Wang et al., Human tumor antigens for cancer vaccine development. Immunol Rev. Aug. 1999;170:85-100.

Wang et al., Role of cytokines in epidermal Langerhans cell migration. J Leukoc Biol. Jul. 1999;66(1):33-9.

Webb et al., Mitogen-induced human lymphocyte activation in serum-free medium. Clin Immunol Immunopathol. Apr. 1973;1(3):304-10.

Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.

Whiteside et al., Antigen-processing machinery in human dendritic cells: up-regulation by maturation and down-regulation by tumor cells. J Immunol. Aug. 1, 2004;173(3):1526-34.

Whiteside et al., Evidence for local and systemic activation of immune cells by peritumoral injections of interleukin 2 in patients with advanced squamous cell carcinoma of the head and neck. Cancer Res. Dec. 1, 1993;53(23):5654-62.

Whiteside, Immunobiology and immunotherapy of head and neck cancer. Curr Oncol Rep. Jan. 2001;3(1):46-55.

Yang et al., The use of polyethylene glycol-modified interleukin-2 (PEG-IL-2) in the treatment of patients with metastatic renal cell carcinoma and melanoma. A phase I study and a randomized prospective study comparing IL-2 alone versus IL-2 combined with PEG-IL-2. Cancer. Aug. 15, 1995;76(4):687-94.

METHOD OF IMMUNOTHERAPY FOR TREATMENT OF HUMAN PAPILLOMAVIRUS INFECTION

RELATED APPLICATIONS

This application is continuation of U.S. application Ser. No. 13/514,688, filed on Jun. 8, 2012, which is a national stage filing under 35 U.S.C. § 371 of international application PCT/US2010/059450, filed Dec. 8, 2010, which claims the benefit under 35 U.S.C. § 119(e) of U.S. provisional application Ser. No. 61/267,590, filed Dec. 8, 2009, the disclosures of all of which are incorporated by reference herein in their entireties.

TECHNICAL FIELD

The present invention relates to methods of reversing immune suppression. In particular, the present invention relates to reversing immune suppression in human papillomavirus (HPV) and treating HPV infection.

BACKGROUND OF THE INVENTION

Human papillomaviruses (HPV) are a family of sexually transmitted DNA viruses with over 100 different genotypes. The genotypes are divided into the low-risk and high-risk categories based on the spectrum of lesions they induce. The low-risk types primarily induce benign genital condylomas and low-grade squamous intraepithelial lesions whereas the high-risk types are associated with the development of anogenital cancers and can be detected in >99% of cervical cancers, with HPV16 found in about 50% of cases. In the United States, an estimated 75% of the sexually active population acquires at least one genital HPV type during their lifetime.

While morbidity and mortality caused by cervical cancer can be reduced with effective Papanicolaou (Pap) smear screening, early detection, and treatment, none of these are readily available in developing countries, the origin of many immigrants to the U.S. In developing countries, cervical cancer remains the second leading cause of cancer-related deaths among women. Importantly, the burden of this disease is expected to increase dramatically in the next decades due to changing demographics. Even in the U.S. where screening programs have reduced the overall rate of invasive cancer, a disparity exists in the incidence of cancer development between white non-Hispanic, black, Hispanic, and economically disadvantaged women. Penetrance of the current FDA-approved preventive vaccine for HPV, GARDASIL® (Merck), in the U.S. has been disappointing. The vaccine was administered to only 25% of girls ages 13-17, 10% of all females ages 18-26, and was given to only 1.1% of Hispanic women in 2007. Moreover, the vaccine is ineffective in women that have already been infected with the virus, whether they have developed (pre-) cancerous cervical lesions or not. Given the lifetime risk of HPV infection and the fact that populations severely underrepresented in vaccine coverage will likely continue to develop cervical and other HPV-related diseases at an alarming rate, it is clear that there is an enormous need for therapeutic approaches that would mitigate carcinogenic effects after viral infection has occurred.

HPV are non-lytic, non-enveloped viruses. Their genome coding regions are denoted E and L for "early" and "late" proteins. The E proteins fulfill regulatory functions vital for genome replication, two of which (E6 and E7) play a significant role in oncogenesis, while the two L proteins (L1 and L2) are the self-assembling capsid proteins responsible for DNA packaging and virion assembly. Infection by papillomaviruses is unique in that its productive lifecycle is coupled to the cellular differentiation of proliferating host epidermal or mucosal basal epithelial cells. HPV remains suprabasal throughout its lifecycle and therefore only contacts cells in the epidermis such as basal cells and Langerhans cells (LC). Due to the coupling of its lifecycle to cellular differentiation, it is difficult to produce HPV virions in vitro. As an alternative to HPV virions, HPV virus-like particles (VLP) and HPV pseudovirions, capable of carrying reporter plasmids, have been developed and are both technologies that are established in the laboratory of Applicants.

Persistence of a high-risk HPV infection is a major risk factor in the development of cervical cancer. While a majority of women infected with HPV clear the virus, the time taken to do so can range from many months to years. About 15% of women that have high-risk HPV infections do not initiate an effective immune response against HPV, allowing the virus to persist for decades. The slow clearance rate and lack of effective immunity indicates that HPV somehow escapes the immune response.

HPV has developed a variety of escape mechanisms that circumvent immediate elimination, allowing viral replication and persistence in the host. Applicants have shown that HPV manipulates LC as a mechanism of immune escape, shown in FIG. 4. LC located in the epithelial layer of the skin and mucosa are the first and critical APC to come into contact with HPV. Consequently, LC are responsible for initiating an effective immune response against HPV infection. Upon recognition of a foreign antigen, LC undergo maturation, which consists of phenotypic and functional changes including up-regulation of co-stimulatory molecules CD80 and CD86, MHC class I and II, chemokine receptors such as CCR7, secretion of cytokines and chemokines, and migration to regional lymph nodes. Applicants have established that LC exposed to HPV16 L1 L2 VLP do not up-regulate co-stimulatory molecules and chemokine receptors, do not secrete cytokines and chemokines and do not initiate epitope-specific immune responses against HPV16 VLP-derived antigens. In contrast, myeloid DC are activated by HPV16 L1 L2 VLP and once activated, stimulate HPV-specific T cells. Different intracellular signaling cascades are initiated in DC versus LC upon uptake of HPV16 L1 L2 VLP. When stimulated with HPV16 L1 L2 VLP, the mitogen-activated protein kinase (MAPK) pathway is activated in DC whereas it is inactivated in LC. However, the phosphoinositide 3-kinase (PI3K) pathway is activated in LC, leading to a signaling cascade that results in the inactivation of Akt. HPV16 E7-specific T cells can recognize and kill LC exposed to HPV16 L1L2-E7 chimeric VLP (cVLP), indicating that HPV peptides are presented by LC after cVLP internalization but that HPV16 L1 L2 VLP inhibit LC from inducing an immune response. Taken together, the data suggest that LC present HPV-derived peptides in the absence of co-stimulation, thereby becoming tolerogenic and immune-suppressive. This in turn can lead to persistence of the HPV infection and an increased likelihood of cancer development.

Prophylactic vaccines for HPV induce high titers of HPV-neutralizing antibodies and have shown high efficacy up to 6.5 years of follow-up and sustained levels of antibodies. However, in women infected with HPV, a phase 3 trial found no evidence of accelerated viral clearance in the vaccinated group as compared to the control group, illustrating conclusively the lack of therapeutic efficacy in preventive VLP-based vaccines. Furthermore, with the long incubation time of HPV, several mechanisms of immune evasion and only a few years of observation, sustained efficacy of prophylactic vaccines on cancer prevention has yet to be determined. The fact that about one third of cervical cancer is caused by HPV types other than those currently present in the vaccines increases the scope of the problem. Thus, it will take decades to be able to detect a quantifiable effect on cervical cancer rates. Meanwhile, the need for therapies to treat HPV infections and associated lesions remains for the hundreds of millions of women worldwide that are currently infected with high-risk HPV or will become infected in the coming years.

Surgery, the standard of care for patients with cervical intraepithelial neoplasia (CIN) lesions, is usually quoted as being up to 90% effective in removing CIN lesions when followed for one year. However, it is less effective when women are monitored over their lifetime. Greater than 80% of women that undergo surgical procedures will subsequently return in need for a second related procedure in cases where surgery does not remove the HPV infection or where elimination of one HPV type encourages re-activation of secondary HPV infections. The therapeutic vaccines that are in development aim to control malignancy by activating the patient's own cellular immune response and target antigens present in the (pre-) cancer cells. Several candidate vaccines have been developed over the last fifteen years; however, to date, there is not a single cancer vaccine that has been approved by the Food and Drug Administration.

Interventions that prevent HPV infections from reaching the stage of inducing carcinogenesis are needed. Such interventions are feasible, since HPV infection can be detected early on with a commercially available HPV detection kit (Digene Corp.).

Several lines of evidence support the importance of the cellular immune system in controlling the pathogenesis of HPV and associated cervical lesions. Firstly, 25-40% of HPV positive, mildly dysplastic lesions resolve spontaneously or shortly after local biopsy suggesting that induction of local inflammation may be involved with regression. Secondly, immunodeficiency is associated with increased incidence of HPV infection. Regressing HPV-associated skin warts and genital warts often have T lymphocytes in the lesions, suggesting that active cell-mediated immune responses to HPV may be a component of regression of the disease. Taken together, these studies illustrate that therapeutic regimens for HPV infection and its associated diseases should aim to induce strong cellular immunity at the site of infection.

Therefore, there is a need for both an effective immunological treatment of HPV over the lifetime of women as well as a method of overcoming the HPV-induced immune suppression of LC that prevents effective treatment.

SUMMARY OF THE INVENTION

The present invention provides a method of treating human papillomavirus (HPV), including the steps of administering a therapeutically effective amount of a primary cell-derived biologic to a patient infected with HPV, and inducing an immune response to HPV infection.

The present invention also provides for a method of overcoming HPV-induced immune suppression of Langerhans cells (LC), including the steps of administering a therapeutically effective amount of a primary cell-derived biologic to a patient infected with HPV, and activating LC.

The present invention provides for a method of increasing LC migration towards lymph nodes, including the steps of administering a therapeutically effective amount of a primary cell-derived biologic to a patient infected with HPV, activating LC, and inducing LC migration towards lymph nodes.

The present invention further provides for a method of generating immunity against HPV, including the steps of administering an effective amount of a primary cell derived biologic to a patient infected with HPV, generating immunity against HPV, and preventing new lesions from developing.

BRIEF DESCRIPTION OF THE DRAWINGS

Other advantages of the present invention will be readily appreciated as the same becomes better understood by reference to the following detailed description when considered in connection with the accompanying drawings, wherein.

DETAILED DESCRIPTION OF THE INVENTION

Figure 1:
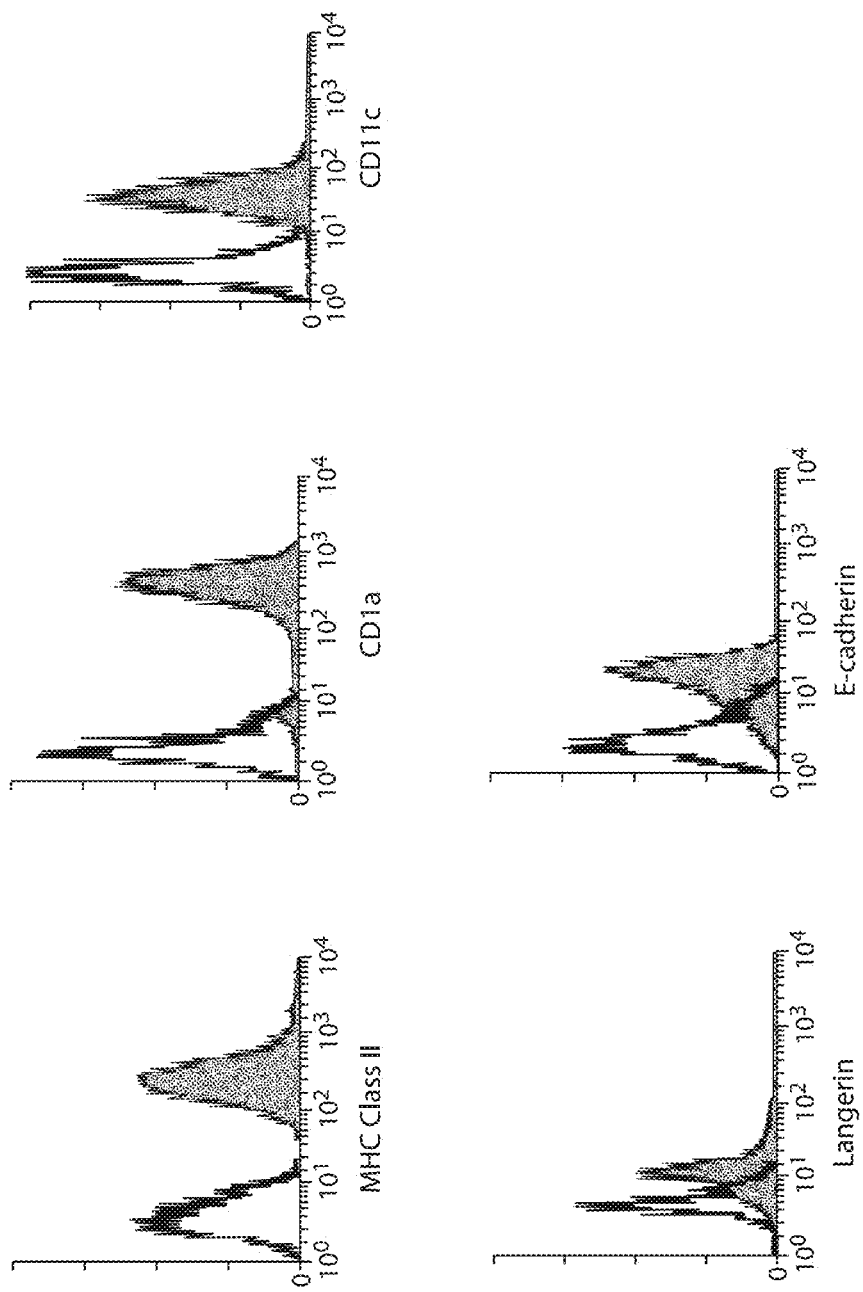
FIG. 1 is a histogram of phenotypic markers expressed in Langerhans cells (LC) (prior art)

The present invention provides in general for methods of treating HPV and overcoming HPV-induced immune suppression of LC by the administration of a primary cell-derived biologic (IRX-2). The treatment of the present invention is effective in treating patients with persistent HPV and whose immune system is not able to produce an effective response against HPV.

As used herein, "effective amount" refers to an amount of primary cell derived biologic that is needed to achieve the desired result of the present invention, namely, producing a reversal of immune suppression of LC in HPV-infected patients. One skilled in the art can determine the effective amount of the primary cell derived biologic that should be given to a particular patient.

"IRX-2", also known as "citoplurikin", is a leukocyte-derived, natural primary cell-derived biologic produced under cGMP standards by purified human white blood cells (mononuclear cells) stimulated by phytohemagglutinin (PHA) and ciprofloxacin (CIPRO). The major active components are interleukin 1β (IL-1β, also referred to herein as IL-1), interleukin 2 (IL-2), interleukin 6 (IL-6), interleukin 8 (IL-8), tumor necrosis factor α (TNF-α), and γ-interferon (IFN-γ). Preferably, the IRX-2 used in the present invention includes these six critical cytokines and can contain only these six critical cytokines. IRX-2 has also previously been referred to as an "NCM", a natural cytokine mixture, defined and set forth in U.S. Pat. Nos. 6,977,072 and 7,153,499. The terms IRX-2, primary cell-derived biologic, and NCM are used interchangeably herein.

Briefly, IRX-2 is prepared in the continuous presence of a 4-aminoquinolone antibiotic and with the continuous or pulsed presence of a mitogen, which in the preferred embodiment is PHA. Other mitogens, however, can also be used. The IRX-2 produced for administration to patients contains a concentration of IL-1β that ranges from 60-6,000 pcg/mL, more preferably, from 150-1,800 pcg/mL; a concentration of IL-2 that ranges from 600-60,000 pcg/mL, more preferably, from 3,000-12,000 pcg/mL, and concentrations of IFN-γ and TNF-α that range from 200-20,000 pcg/mL, more preferably, from 1,000-4,000 pcg/mL.

IRX-2 can also contain a concentration of IL-6 that ranges from 60-6,000 pcg/mL, more preferably, from 300-2,000 pcg/mL; a concentration of IL-8 that ranges from 6000-600,000 pcg/mL, more preferably from 20,000-180,000 pcg/mL; a concentration of TNF-α that ranges from 200-20,000 pcg/ml, more preferably, from 1,000-4,000 pcg/mL. Recombinant, natural or pegylated cytokines can be used, or IRX-2 can include a mixture of recombinant, natural or pegylated cytokines. IRX-2 can contain only the above cytokines; however, other cytokines can be included. The IRX-2 of the present invention can further include other recombinant, natural or pegylated cytokines such as IL-7, IL-12, IL-15, GM-CSF (at a concentration that ranges from 100-10,000 pcg/mL, more preferably from 500-2,000 pcg/mL), and G-CSF. The method of making IRX-2 is disclosed in the above-cited patents as well as in U.S. patent application Ser. No. 12/423,601.

Also encompassed by the present invention are derivatives, fragments and peptides related to the cytokines disclosed herein, wherein such derivatives, fragments and peptides retain the biological activity of their respective cytokines.

The multiple active cytokine components of IRX-2 act on multiple cell types of the immune system, including T cells and dendritic cells. In clinical trials of H&NSCC patients, IRX-2 was shown to be safe, tolerable and biologically active, resulting in both apparent disease-free survival and overall survival. The physiologic quantities of cytokines in IRX-2 can be administered locally, including topically, providing an opportunity to alter the microenvironment where LC encounter HPV. Natural cytokine mixtures from monocyte-conditioned medium or mixtures of recombinant inflammatory cytokines containing TNFα, IL-1β, IL-6, and PGE2 have traditionally been used to mature DC for ex vivo generated DC-based cancer vaccines. The physiologic cytokine levels in IRX-2 are much lower than concentrations of recombinant cytokines used in ex vivo DC maturation or in high dose systemic cytokine therapies. The low levels of cytokines in IRX-2 allow it to be injected directly into patients with no significant toxicity.

IRX-2 also contains several cytokines that are critical mediators of T cell activation and proliferation. The ability of IRX-2 to activate both DC and T cells makes it especially attractive since it is this combination of immune cell subsets that coordinate the immune response against virus-infected cells.

Other compounds can also be administered along with IRX-2, such as chemical inhibitors, non-steroidal anti-inflammatory drugs (NSAIDS), zinc, and combinations thereof.

The chemical inhibitor can be any chemotherapeutic agent that is not immunosuppressive (preferably used at low doses) and that has immunomodulatory effects so as to increase immunity and/or an immune response, e.g., by inhibiting immune suppression or suppressor mechanisms in the body. According to a preferred embodiment, the chemical inhibitor is an anti-neoplastic agent, including but not limited to alkylating agents, antimetabolites and antibiotics. The chemical inhibitor can also be an immunomodulating agent such as thalidomide. The chemical inhibitor can also be in a salt or other complex form. Preferably, the chemical inhibitor is the alkylating agent cyclophosphamide (CY).

The NSAID is preferably indomethacin (INDO), which is both a CoxI and CoxII inhibitor. The NSAID can also be ibuprofen or CoxII inhibitors such as celecoxib and rofecoxib, or combinations thereof.

The four components used together (i.e. chemical inhibitor, NSAID, primary cell derived biologic, and zinc) are able to address the suppressive environment created by the immune target and restore the cellular immune response of the patient. More specifically, the chemical inhibitor inhibits T regulatory cells; the NSAID reverses local immune suppression by prostaglandins, the primary cell derived biologic activates dendritic cells, stimulates T cells, and protects T cells from apoptosis; and zinc provides key nutrients for T cell function. This combined action encourages immune response to both endogenous and exogenous antigens.

More specifically, the present invention provides for a method of treating HPV, by administering a therapeutically effective amount of IRX-2 to a patient infected with HPV, and inducing an immune response to HPV. Preferably, IRX-2 includes the six critical cytokines of IL-1, IL-2, IL-6, IL-8, TNF-α, and IFN-γ as described above. Additional cytokines can also be included as described above. Additional compounds such as a chemical inhibitor, NSAID, and zinc can also be administered as described above. Preferably, the IRX-2 is administered in the epithelium by injection where HPV infection is present as well as where the LC are located that are needed to induce an immune response. Topical application to the cervix is also preferred. Topical application methods include, but are not limited to, the dispersal of IRX-2 in the liposome formulation Biphasix™ (Helix Biopharma Corp., Aurora, Ontario, CA), followed by application to cervical epithelium; use of the Cervical Drug Delivery System™ (Cytocore®, Inc. Chicago, Ill.), wherein IRX-2 is absorbed into a bioadhesive polymer patch, which is then affixed to cervical epithelium; and the infusion of IRX-2 solution into the cervix via a cervical isolation and delivery apparatus such as that disclosed in U.S. Pat. No. 7,165,550 to Tracy et al.

In general, IRX-2 acts to effectively "turn on" the immune system by maturing immature dendritic cells, stimulate the production of naïve T cells, and effectively present antigen to the naïve T cells. IRX-2 is able to effectively treat HPV by inducing an immune response to HPV, something that is lacking in HPV patients due to the immune suppressive actions of HPV on LC.

Figure 3:
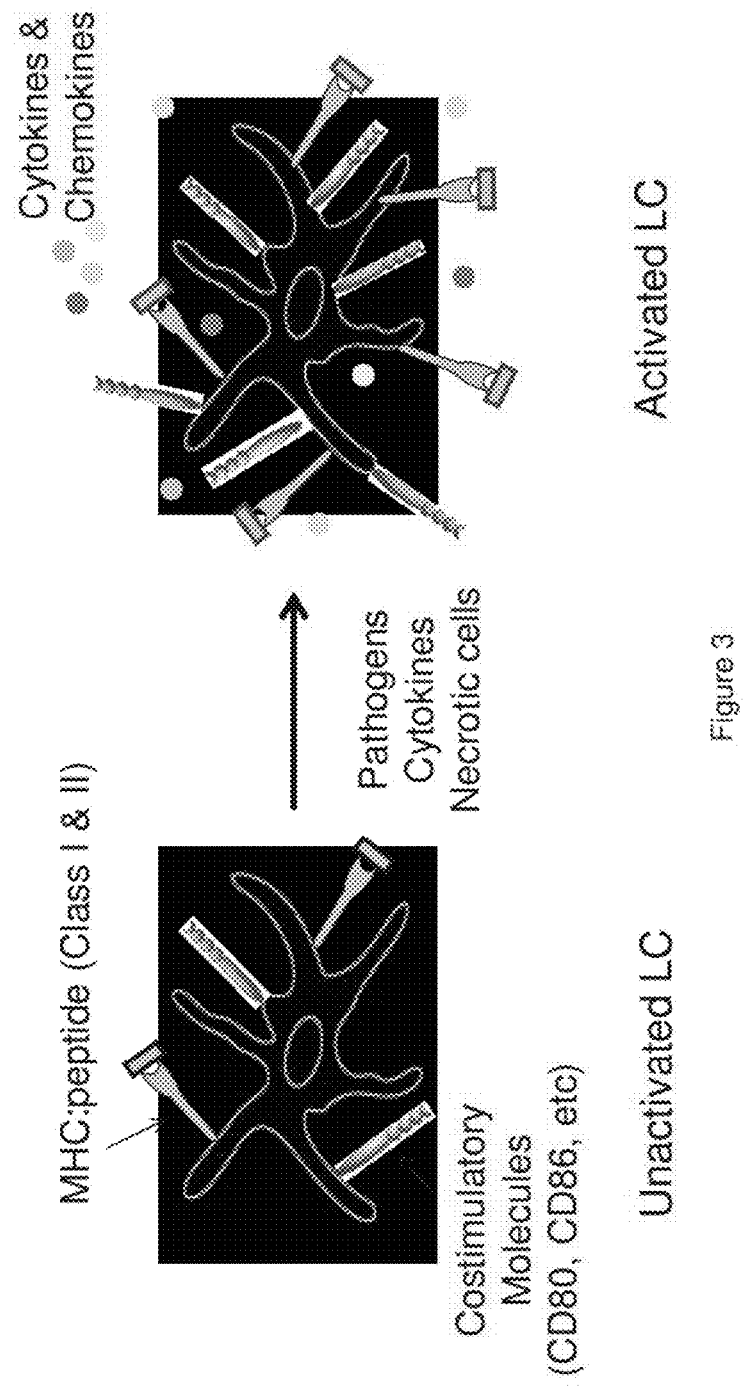
FIG. 3 is a diagram of unactivated LC versus activated LC.
Figure 4:
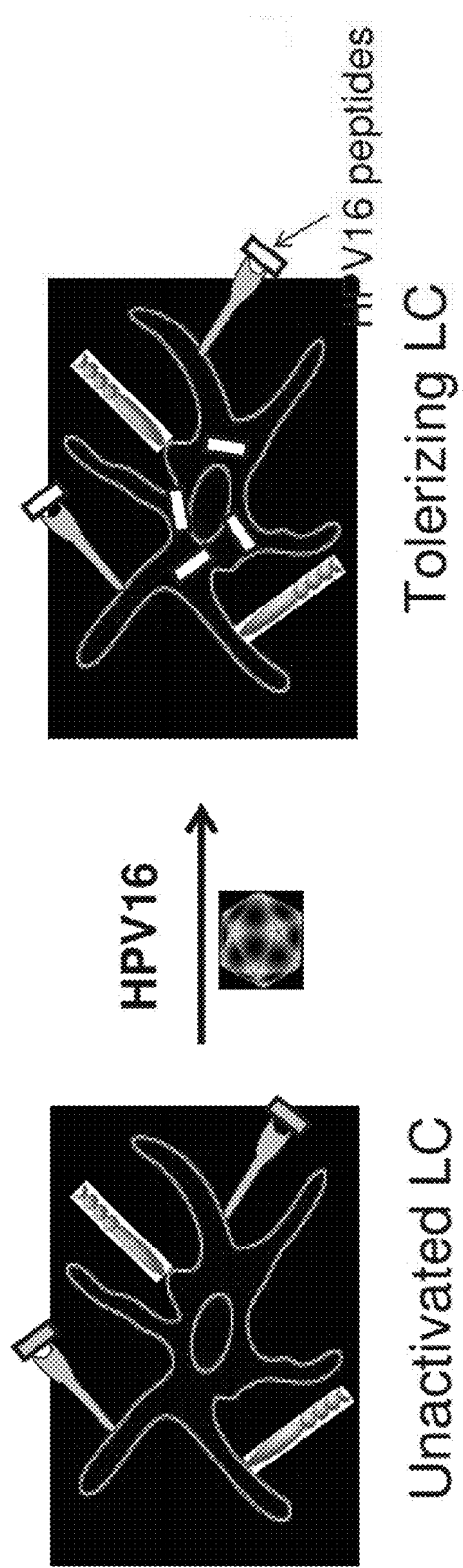
FIG. 4 is a diagram of HPV inducing tolerization of LC.

The immune response to HPV is induced by activating LC. Activated versus unactivated LC are shown in FIG. 3. Essentially, IRX-2 is able to overcome the immune suppression of LC by HPV. Activated LC can then secrete T cell-activating and immune modulating cytokines in order to induce an immune response to HPV, thus eliminating all present lesions as well as protecting against the eruption of future lesions due to the ability of the immune system to effectively attack HPV. For example, IRX-2 increases secretion of IL-8 and ILIP-10 production by LC. The LC are able to activate HPV-specific CD8+ T cells. As described in the examples below, activation of LC is confirmed by an upregulation of CD1a, MHC class I, MHC class II, CD40, CD80, CD83, CD86, and CCR7.

The present invention also provides for a method of overcoming HPV-induced immune suppression of LC, by administering a therapeutically effective amount of IRX-2 to a patient infected with HPV, and activating LC. The IRX-2 is described above. By activating LC, the IRX-2 is able to overcome immune suppression of LC due to HPV. Thus, the LC can now effectively induce the activation of T cells to attack the HPV present in the patient.

The present invention provides for a method of increasing LC migration towards lymph nodes, by administering a therapeutically effective amount of IRX-2, activating LC, and inducing LC migration towards lymph nodes. The IRX-2 is described above. Active LC can effectively migrate towards a patient's lymph nodes after IRX-2 treatment and produce an immune response in a patient suffering from HPV. Due to immune suppression by HPV, LC are normally not able to migrate to the lymph nodes. However, treatment with IRX-2 reverses this immune suppression so that LC are able to effectively function in the immune system.

The present invention provides for a method of generating immunity against HPV, by administering an effective amount of IRX-2 to a patient infected with HPV, generating immunity against HPV, and preventing new lesions from developing. IRX-2 is able to activate LC which have been suppressed by HPV. Activated LC can generate an immune response to HPV. Having an immune system that actively recognizes and is able to attack HPV allows for the prevention of any new lesions from developing. An activated immune system is able to effectively treat HPV and prevent future development of the disease.

There are several benefits to the present invention. Since lesions are primarily caused by persistence of HPV, interventions that induce immunological clearance of infections and prevent the transmission of HPV can have an enormous impact on public health. Elimination of HPV persistence contributes to reduced health care spending for each HPV-related cancer that would have occurred. This approach is a low-cost alternative to repeated screening or expensive surgical intervention with a high reasonable expectation of success, because it targets the cause of HPV-induced lesion development, namely HPV persistence and its related immune escape.

For any of the above embodiments, the following administration details and/or protocols for treatment are used:

Preferably, the cytokine composition is applied locally by injection to HPV-infected epithelium. Alternatively, the cytokine composition of the present invention can be injected around lymphatics that drain into lymph nodes regional to a lesion or other virus infected area being treated. More specifically, local perilymphatic injections or other injections that are known to those of skill in the art are administered to provide sufficient localization of the immunotherapy preparation.

In the embodiment wherein an exogenous antigen is to be utilized, exogenously provided synthetic or extracted antigens such as tumor antigen and peptides (see Bellone, 1998) can be administered into the pre-primed or co-primed regional or distal lymph node, either in a separate preparation or as part of the cytokine composition of the invention.

Endogenous suppression of T cells, which can be caused by, e.g., cancer or other immunosuppressive diseases, can be blocked by the co-administration of low dose cyclophosphamide (CY) and a non-steroidal anti-inflammatory drug (NSAID) (i.e., in combination with the cytokine compositions of the invention). The NSAID is preferably indomethacin (INDO) but ibuprofen or CoxII inhibitors such as celecoxib (CELEBREX®) or rofecoxib (VIOXX®) or combinations thereof can also be used. Side effects of NSAIDS can be aggressively treated with proton inhibitors and prostaglandin E analogs. Zinc and multi-vitamins, possibly including the addition of selenium, can also be added as agents to help restore T cell immunity. Preferably, the dose of zinc is 15 to 75 mg. A standard multivitamin can be administered. The zinc can be an available gluconate.

The cytokine compositions of the invention can be administered prior to or after surgery, radiotherapy, chemotherapy, or combinations thereof. The compositions of the invention can be administered during the recurrence of tumors, i.e., during a period where tumor growth is occurring again after a period where tumors were thought to have disappeared or were in remission.

The Mechanism of Action of IRX-2.

As defined above, the primary cell-derived biologic of the invention acts as an adjuvant, i.e., stimulates or enhances the immune response of a patient to a particular antigen. Moreover, the IRX-2 compositions and methods of the invention are particularly suited to stimulate T cell-mediated immune responses. Immune responses promoted by the compositions and methods of the invention include the induction or generation of naïve T cells, the differentiation and maturation of dendritic cells, allowing for proper presentation of antigen to T cells (e.g., in the lymph nodes), and the activation of monocytes and macrophages. Specifically, in cancer patients, immune responses promoted by the compositions and methods of the invention include tumor infiltration by lymphocytes, tumor fragmentation and regression as well as a reduction in sinus histiocytosis (when present). Essentially, the primary cell-derived biologic induces immune production and blocks immune destruction. The mechanism of action of the primary cell-derived biologic is further described in U.S. patent application Ser. No. 12/323, 595 to Applicants.

More specifically, the compositions and methods of the present invention aid in overcoming immune depression/suppression in patients by inducing the production of naïve T cells. The term "naïve" T cells, as defined herein, denotes newly produced T cells, which T cells have not yet been exposed to antigen. Thus, the compositions and methods of the invention replenish or generate new T cells.

Because dendritic cells are known to play such a key role in antigen presentation in the production of an appropriate immune response in vivo, an agent having a stimulatory effect on dendritic cell maturation will act as an adjuvant in eliciting a good immune response to an antigen. The cytokine compositions of the present invention promote dendritic cell maturation. The cytokine compositions of the invention also provide a further adjuvant effect by acting as potent activators of monocytes/macrophages. Monocytes are precursors to both DCs and macrophages in the body and thus an agent that promotes monocyte/macrophage activation has an adjuvant effect on immune responses in vivo.

The primary cell-derived biologic also blocks immune destruction by protecting the activated T cells from apoptosis. Clinical and experimental data show that certain cytokines, especially survival cytokines using the common receptor γ chain, are able to protect activated T cells from tumor-induced death and enhance their anti-tumor activity.

More specifically, there are several ways in which the primary cell-derived biologic protects T cells from apoptosis. The expression of anti-apoptotic signaling molecules (i.e. JAK-3 and phosphor-Akt) is up-regulated and the expression of pro-apoptotic molecules (i.e. SOCS-2) is down-regulated. Activation of caspases in CD8+ and CD4+T lymphocytes is decreased and cFLIP expression is increased. Inhibition of the PI3K/Akt survival pathway is counteracted by IRX-2. The T cells are protected from both extrinsic apoptosis (MV-induced and FasL-induced apoptosis) and intrinsic mitochondrial apoptosis.

The protection from extrinsic MV-induced apoptosis is further accomplished by preventing down-regulation of JAK3, CD3-ζ, and STAT5; inhibiting dephosphorylation of Akt-1/2; and maintaining balanced ratios of Bax/Bcl-2, Bax-Bcl-xL, and Bim/Mcl-1. The protection from MV-induced apoptosis is also accomplished by preventing induction of the activity of caspase-3 and caspase-7. More specifically, the induction of the active cleaved form of caspase-3 is blocked, as is the loss of mitochondrial membrane potential. Nuclear DNA fragmentation is inhibited. Protection from intrinsic apoptosis by the primary cell-derived biologic is shown by its protection of activated T cells from staurosporine-induced apoptosis.

Importantly, the cytokines of the primary cell-derived biologic protect the activated T cells from apoptosis in a synergistic manner. In other words, the combination of the cytokines in the primary cell-derived biologic produces a greater effect than is seen by administering individual cytokines alone.

In view of the above, the compositions and methods of the present invention stimulate the immune system via multiple effects, including the in vivo maturation of dendritic cells resulting in effective peptide antigen presentation as well as activation of monocytes and macrophages and the production of naïve uncommitted T cells. The proper presentation of antigen leads to T and B cell clonal expansion, creating immunity in the patient. In the case of cancer patients, the effects noted above result in the infiltration, e.g., of lymphocytes, into tumors (e.g., via hematogenous spread) and tumor reduction and/or destruction. The result is increased survival due to immunologic memory.

The cytokine compositions of the present invention are administered and dosed to promote optimal immunization either to exogenous or endogenous antigen, taking into account the clinical condition of the individual patient, the site and method of administration, scheduling of administration, patient age, sex, and body weight. The pharmaceutically "effective amount" for purposes herein is thus determined by such considerations as are known in the art. The amount must be effective to promote immunization, leading to, e.g., tumor reduction, tumor fragmentation and leukocyte infiltration, delayed recurrence or improved survival rate, or improvement or elimination of symptoms, including increased T cell counts.

In the methods of the present invention, the compositions of the present invention can be administered in various ways. It should be noted that the cytokines or exogenous antigens used in the compositions of the invention can be administered in their standard forms or as pharmaceutically acceptable derivatives and can be administered alone or as active ingredients in combination with pharmaceutically acceptable carriers, diluents, adjuvants and vehicles. Furthermore, the compositions of the invention can be administered intra- or subcutaneously, or peri- or intralymphatically, intranodally or intrasplenically or intramuscularly, intraperitoneally, and intrathoracically. The compositions of the invention can also be applied topically to HPV-infected epithelium, for example by infusion into the cervix of a patient. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. When administering the compositions of the present invention, they are generally formulated in a unit dosage injectable form (e.g., solution, suspension, or emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, or vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for the compositions of the invention. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it is desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent or additive used would have to be compatible with the cytokines or exogenous antigens of the invention.

Sterile injectable solutions can be prepared by incorporating the cytokines or exogenous antigens utilized in practicing the present invention in the required amount of the appropriate solvent with several of the other ingredients, as desired.

A pharmacological formulation of the present invention can be administered to the patient in an injectable formulation containing any compatible carrier, such as various vehicles, additives, and diluents; or the cytokines and/or exogenous antigens utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include those disclosed in U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

It should be apparent that the compositions and methods of the invention are useful for the treatment of antigen-producing diseases such as cancer, infectious diseases or persistent lesions, as discussed above. The compositions and methods promote immunization against the antigens produced by these diseases by stimulating immune responses in patients in vivo, which immune responses help to alleviate or eliminate the symptoms and effects of the disease in the patient.

The invention is further described in detail by reference to the following experimental examples. These examples are provided for the purpose of illustration only, and are not intended to be limiting unless otherwise specified. Thus, the present invention should in no way be construed as being limited to the following examples, but rather, be construed to encompass any and all variations which become evident as a result of the teaching provided herein.

Example 1

Generation of Human LC

As HPV only infects human beings, human immune cells were used to study the interaction of HPV with LC. Primary LC that were isolated from human skin, becoming activated through the migration process and express high levels of MHC and costimulatory molecules. Therefore, it is not feasible to isolate primary unactivated skin-derived LC from human donors with which to conduct meaningful in vitro long term and reproducible functional studies. For the experiments, primary LC were generated from peripheral blood monocytes isolated from healthy donors using differentiating cytokines ex vivo. Circulating monocytes were direct precursors of epidermal LC in vivo. Applicants and others have shown that ex vivo derived LC express the same surface markers as epidermal LC (Langerin, E-cadherin, CD11c, CD1a, high MHC class II and intracellular Birbeck granules) (FIG. 1) and can be used consistently for in vitro LC studies.

FIG. 1 shows that human monocyte-derived Langerhans cells express similar phenotypic markers as skin-derived Langerhans cells. Immature Langerhans cells were differentiated from adherent monocytes in 1000 IU/mL GM-CSF, 1000 IU/mL IL-4 and 10 ng/mL TGFβ for 7 days. Cells were analyzed by flow cytometry for the expression of MHC class II (HLA-DP,DQ,DR), CD1a, CD11c, Langerin, or E-cadherin (gray shaded histograms). Isotype controls are shown as black unshaded histograms. Data are representative of LC derived from several healthy donors.

Reversal of HPV Immune Escape

Figure 2:
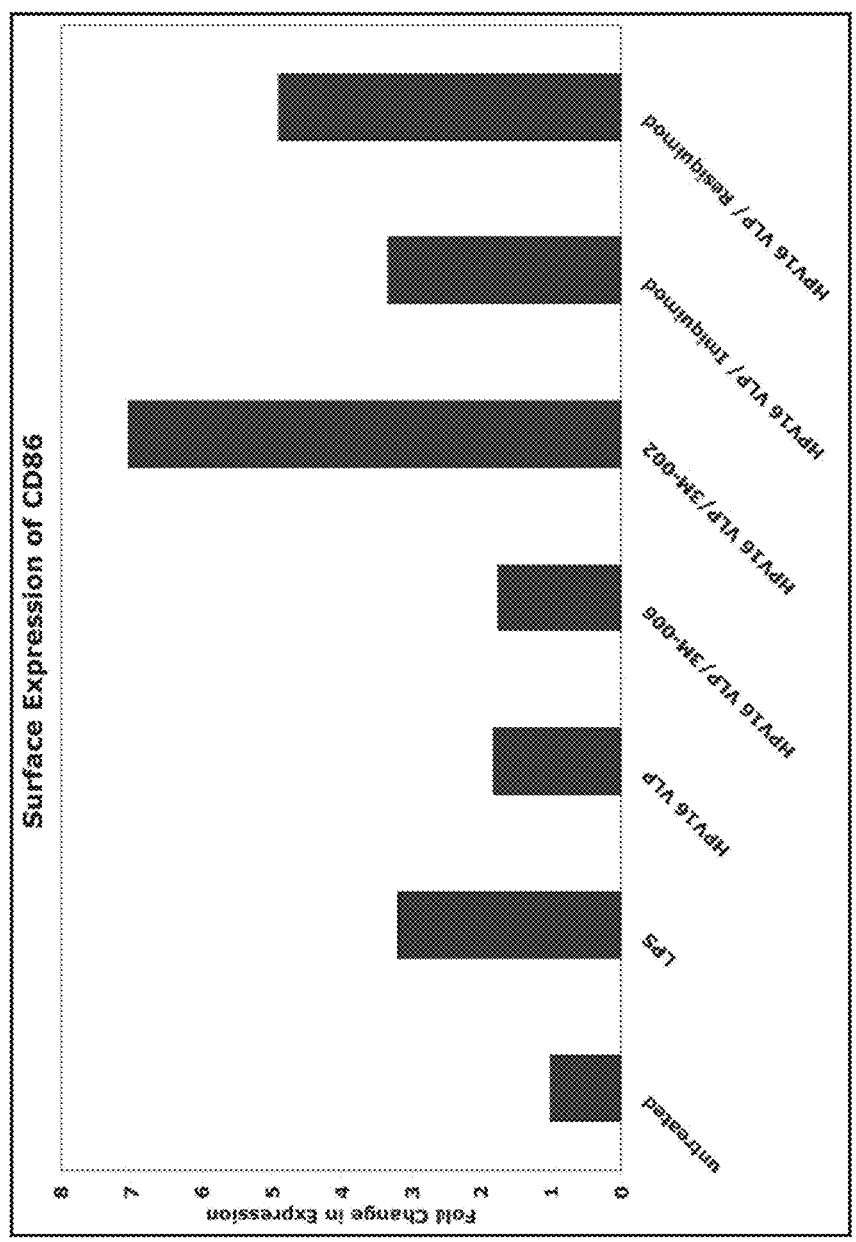
FIG. 2 is a graph showing CD86 expression by LC (prior art)

Applicants have previously embarked on strategies to reverse HPV immune escape by targeting LC. LC express a variety of TLRs, including TLR3, 7, 8, and 9, which recognize pathogen-associated molecular patterns (PAMPs) and upon engaging their ligands activate the cell. Surprisingly, it was found that a TLR 7 agonist ALDARA® (Imiquimod, Graceway Pharmaceuticals, LLC), FDA-approved for external genital warts, had absolutely no effect on LC activation, as measured by expression of CD86 (FIG. 2). This might explain the yet unpublished observations that the use of Imiquimod for treating cervical lesions is not effective. Interestingly, a TLR 8 activator (3M-002) and a TLR7/8 agonist (Resiquimod) fully activated HPV infected LC such that they started to induce HPV-specific T cell responses in vitro. These data indicate that suppression of LC function by HPV can be reversed by activating certain "danger signal" pathways.

Activation of Human Langerhans Cells with IRX-2

The ability of LC to efficiently stimulate T cells after migration from the epidermis to the draining lymph nodes after exposure to pathogens or other "danger signals" requires the expression of costimulatory molecules and chemokine receptors on their cell surface. The effect of IRX-2 on the phenotypic maturation of human monocyte-derived LC in vitro was examined. IRX-2 treatment was found to induce upregulation of both MHC class I and MHC class II, and the costimulatory molecules CD40, CD80 and CD86, the maturation marker CD83, and LC activation was performed as previously described. Briefly, LC were harvested, washed, and either left untreated or treated with HPV16L1L2 VLP at a concentration of 10 μg/106 cells for 1 hour at 37° C. Following the incubation, the cells were placed at 37° C. for 6 hours in complete medium. Next, the cells were left untreated or treated with IRX-2 (1:2 dilution) or with 1 μg/mL LPS as a positive control. The cells were incubated for an additional 48 hours post IRX-2 treatment. Cells were harvested, washed, and stained for flow cytometric analysis staining for CD1a, MHC class I, MHC class II, CD40, CD80, CD83, CD86, or isotype controls. The fold change of surface markers between treatment groups were calculated from MFI values. Increased MFI indicates upregulation of markers and activation of LC. Data are representative of three individual donors The source of IRX-2 was supernatant collected from human peripheral blood mononuclear cells stimulated by phytohemagglutinin (PHA) for a 24-hour period. QC testing was used to test levels of cytokines in the mixture and standardize according to the levels of four key cytokines. The cGMP manufacturing process yielded a highly consistent product with very similar cytokine concentrations from lot to lot. To ensure consistency in LC activation by IRX-2, two different lots of IRX-2 were used to activate LC.

Figure 6:
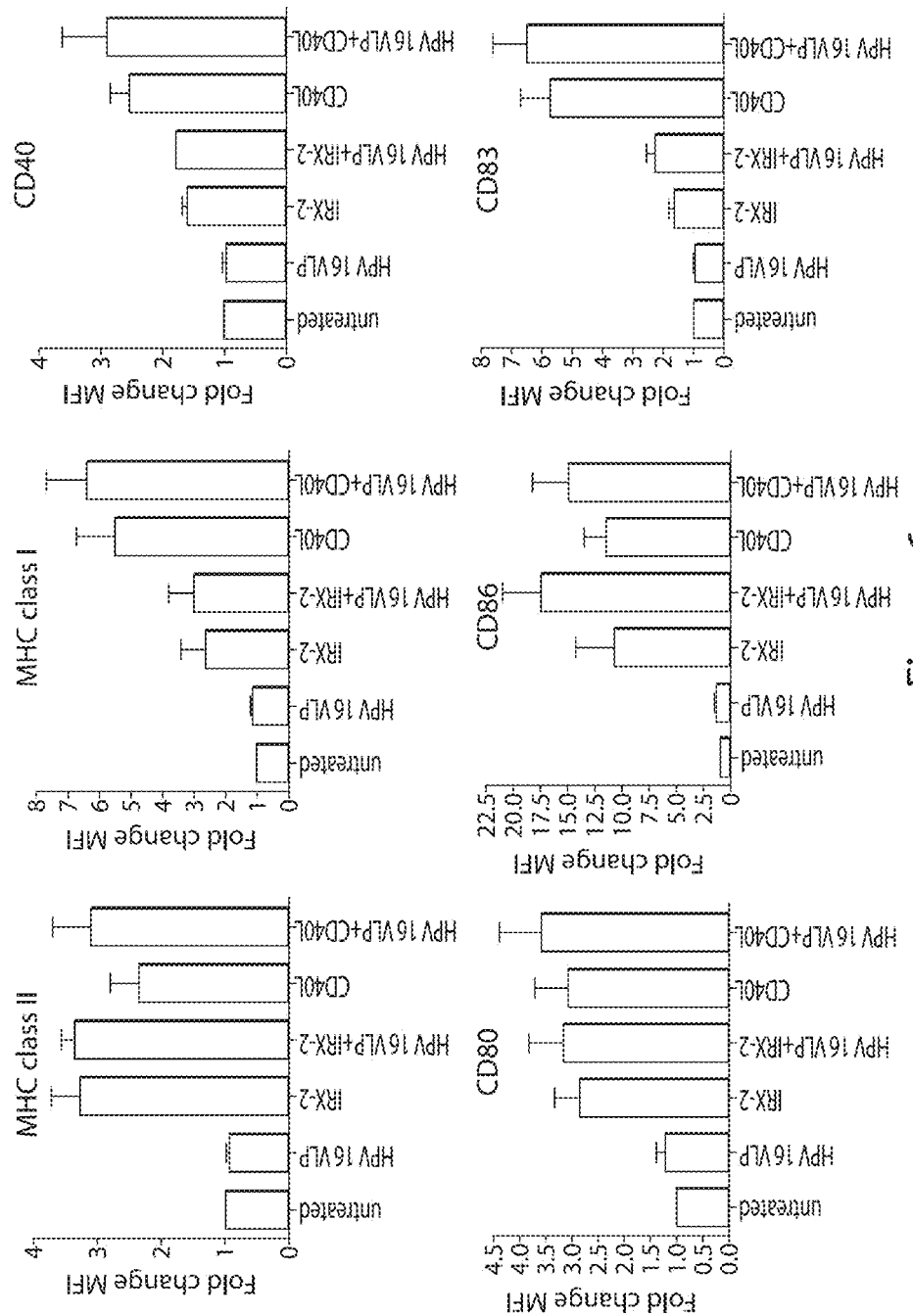
FIG. 6 is a graph of upregulation of surface activation markers on human LC exposed to HPV16 and IRX-2.

As shown in FIG. 6, expression of all six LC markers was strongly elevated by IRX_2 treatment, regardless of whether the LC had been exposed to HPV16 L1 L2 VLP. Interestingly, elevation of the costimulatory molecule CD86 was even more effective in HPV16 LIL2 VLP exposed LC than in controls. Greater than 95% of cells expressed CD86 and greater than 80% of LC expressed the maturation marker CD83 (not shown).

The results indicate that that IRX-2 is a potent inducer of LC activation and maturation, and that its effectiveness is not impaired by prior exposure of LC to HPV.

Example 2

Establishing whether IRX-2, which is currently available for clinical use, can activate LC previously exposed to HPV16 is necessary. The effect of IRX-2 on LC expression of activation markers was reported in Example 1, In the next experiments, the strength of IRX-2 was tested by measuring cytokine secretion, migration, and activation of alloantigen-specific T cells.

Activation of APC, like LC, is required for successful interaction with and activation of primary T lymphocytes. Inflammatory cytokines have the ability to activate APC, resulting in maturation and an increase in antigen-presenting function. IRX-2 is a promising immune modulator that has the potential to influence the immunostimulatory capacity of LC when applied locally to HPV-infected epithelium. In order to determine whether IRX-2 phenotypically and functionally activates LC exposed to HPV, cytokine/chemokine secretion and migration as well as the ability to stimulate alloantigen-specific T cell responses was performed. These studies defined IRX-2 as able to reverse the immune suppression by HPV, similar to TLR8 agonists.

Figure 5:
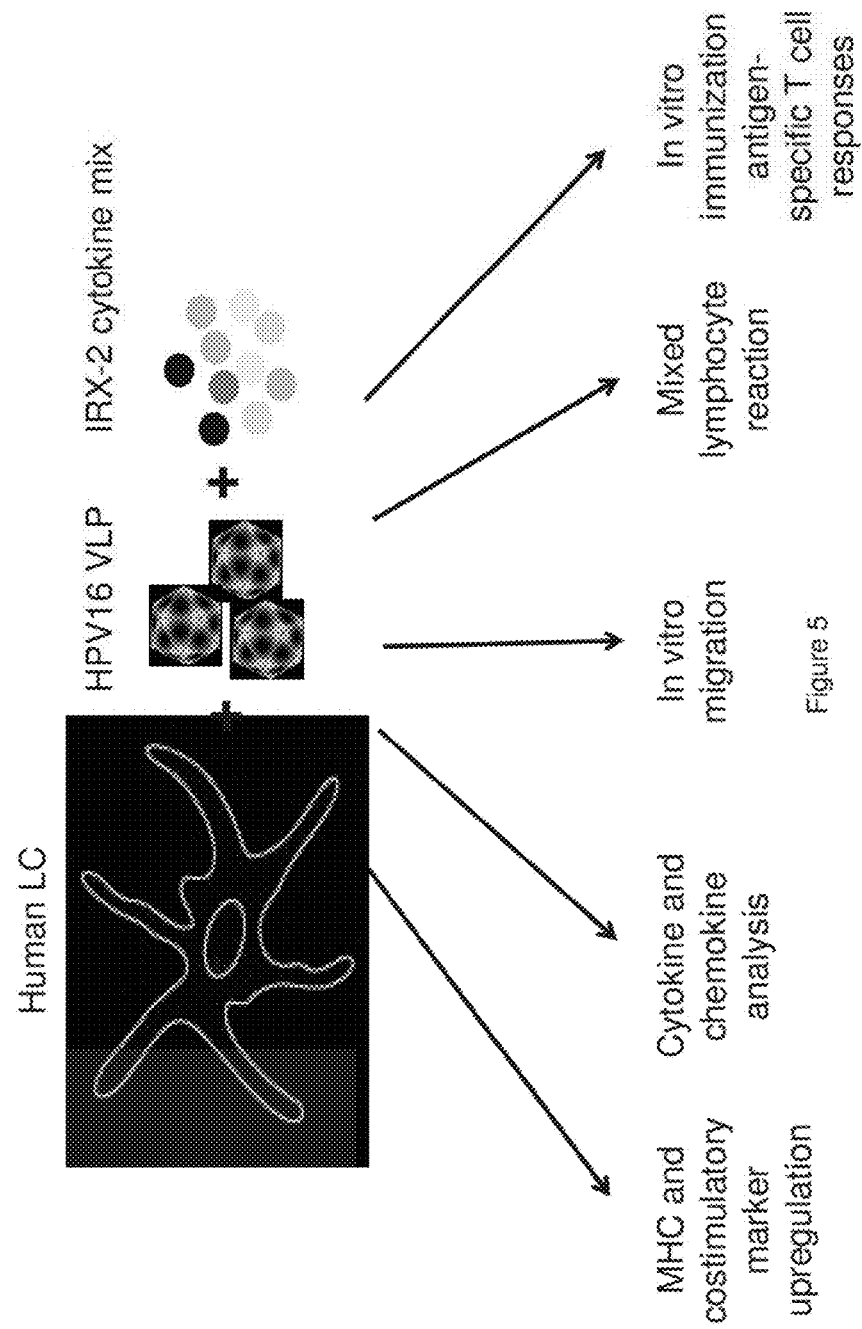
FIG. 5 is a diagram of the experimental design of experiments on LC activation.

Experimental Design:

LC expression levels of T cell co-stimulatory markers was determined when LC were exposed to HPV16 and then to IRX-2. LC were differentiated from peripheral blood monocytes isolated from healthy donors. LC were exposed to HPV16 virus-like particles (VLP) for 6 hours, and then IRX-2 added for an additional 48 hours, as shown in FIG. 5. Cell surface molecules were measured by flow cytometry using fluorescent antibodies. Cell culture supernatants were tested for the presence of immune-stimulatory cytokines and chemokines to determine whether LC have become activated and are secreting T cell-activating or other immune modulating cytokines. LC migration after exposure to HPV VLP and IRX-2 was measured by in vitro migration through a transwell membrane. The capacity to stimulate T cells was evaluated by culturing LC with allogeneic T cells in a mixed lymphocyte reaction (MLR). Untreated LC, LC exposed to HPV VLP alone, and LC treated with IRX-2 alone serve as controls in each experiment. Each experiment was repeated at least 3 times using LC derived from individual healthy donors. Subjects were chosen who are HLA-A*0201 positive, so that well defined T cell immune responses were measured against known HPV-derived peptide antigens. These data show that IRX-2 enables HPV-exposed LC to gain back their capacity to stimulate T cells and to migrate—both functions needed for a productive anti-viral immune response.

Generation of Human Langerhans Cells:

Primary LC were generated from commercially available peripheral blood monocytes isolated by leukapheresis of anonymous healthy donors using differentiating cytokines ex vivo. Monocyte-derived LC were generated first through plastic adherence of cryopreserved PBMC to culture flasks. Adherent cells were cultured for 7 days in medium containing 1000 U/mL recombinant human (rhu)-GM-CSF, 1000 U/mL rhu-IL-4 and 10 ng/mL rhu-TGF-β1, replenished twice during the culture period.

Figure 7:
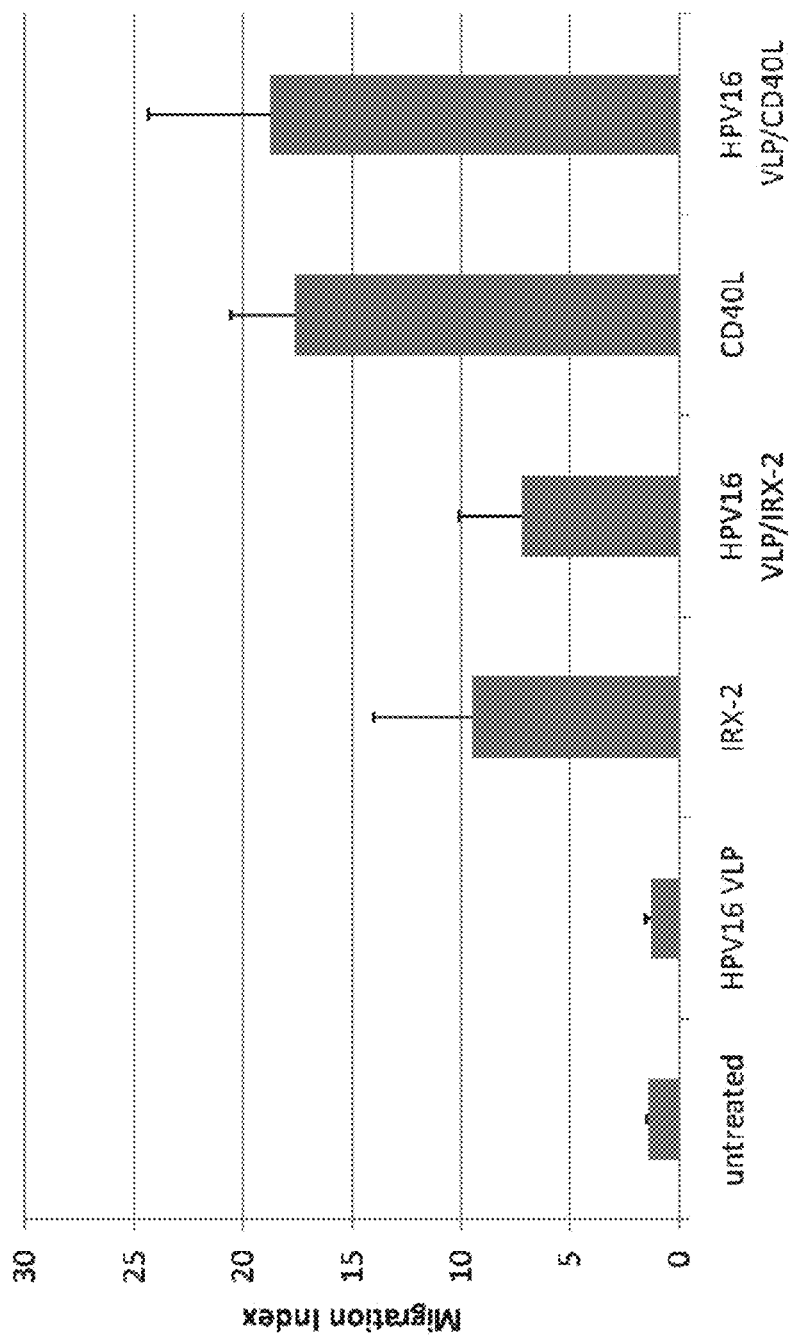
FIG. 7 is a graph showing that IRX-2 induces human LC migration in the absence and presence of HPV16.

LC Migration:

Chemokine directed migration of LC was carried out using 24-well Transwell plates with 5 μm-pore-size polycarbonate filters (Corning Costar). Media was added to the lower chamber containing either 250 ng/ml rhu CCL21 (R&D Systems) or medium alone to control for spontaneous migration. LC untreated or treated as described above, were added to the upper chamber and incubated for 4 hours at 37° C. The cells that migrated to the lower chamber were counted using a hemacytometer or automated cell counter, and CCL21-dependent migration was calculated as the ratio of cells that migrated with CCL21 to cells that migrated without CCL21, termed migration index. Increased migration index indicated a functional activation of LC to move from the tissue towards draining lymph nodes (FIG. 7).

IRX-2 treatment produced a three to four fold increase in migration in both control and HPV L1 L2 VLP. The results indicate that IRX-2 can promote the migration of LC to regional lymph nodes, even when the LC had been exposed to HPV.

Figure 8:
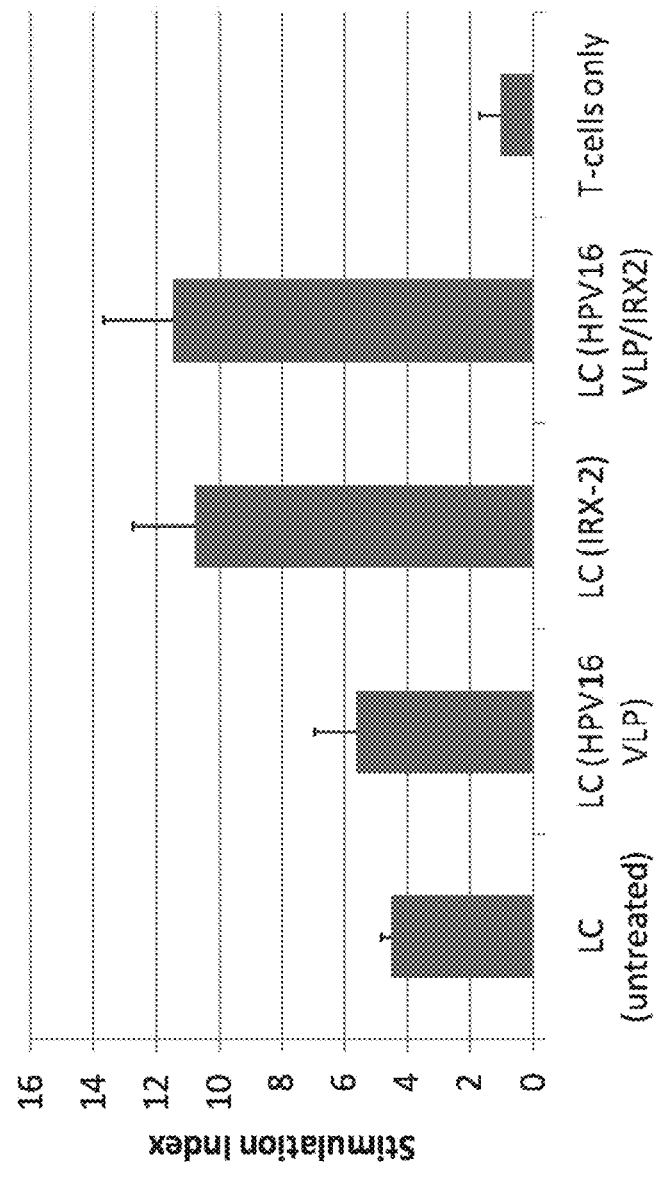
FIG. 8 is a graph showing that human Langerhans cells exposed to IRX-2 are superior in stimulating allogeneic T cells in the presence of HPV.

Mixed Lymphocyte Reaction Assay:

LC were treated with HPV16 L1 L2 VLP and IRX-2 as described above. LC were co-cultured with untouched allogeneic T cells isolated using a MACS negative selection human pan T cell isolation kit. Responder T cells and stimulator LC were cultured at R:S ratios of 10:1 and 5:1 for 5 days. T cells cultured alone, LC cultured alone, T cells cultured with autologous PBMC and T cells cultured with the T cell mitogen PHA served as controls for the assay. Radioactive $^3$H-thymidine-pulsed cells were harvested and radioactivity counted on a scintillation plate counter. Radioactive cpm were determined and compared between treatments. Increased thymidine incorporation was indicative of greater T cell proliferation. Increased T cell proliferation after HPV16 L1L2 VLP exposure and IRX-2 stimulation confirmed that HPV16 L1L2 VLP-exposed LC were gaining back their immunostimulatory capacity in the presence of HPV (FIG. 8).

Cytokine and Chemokine Analysis:

Supernatants were collected from LC stimulated with IRX-2 and tested for secreted cytokine and chemokines. LC were treated as described above. LC were washed 36 hours post IRX-2 treatment and cultured for an additional 36 hours, prior to collection of supernatants. This eliminated measurement of cytokines present in IRX-2 mixture. The assays were completed using the Bio-Plex Suspension Array System which allowed for several inflammation and T cell stimulating and chemoattracting analytes to be assayed at once. The assayed cytokines and chemokines included IL-8, IFN-γ Inducible Protein 10 (IP-10), Monocyte Chemoattractant Protein (MCP)-1, Macrophage Inflammatory Protein (MIP)-1α, MIP-1β, and RANTES. Data were analyzed by comparing the cytokine and chemokine concentrations in the supernatants of treatment groups. Increased Th1-associated cytokine and chemokine secretion indicates functional activation of LC that would support the induction of CD8+ T cell responses, while increased suppressive cytokines suggests a tolerizing or suppressive function of LC.

Figure 9:
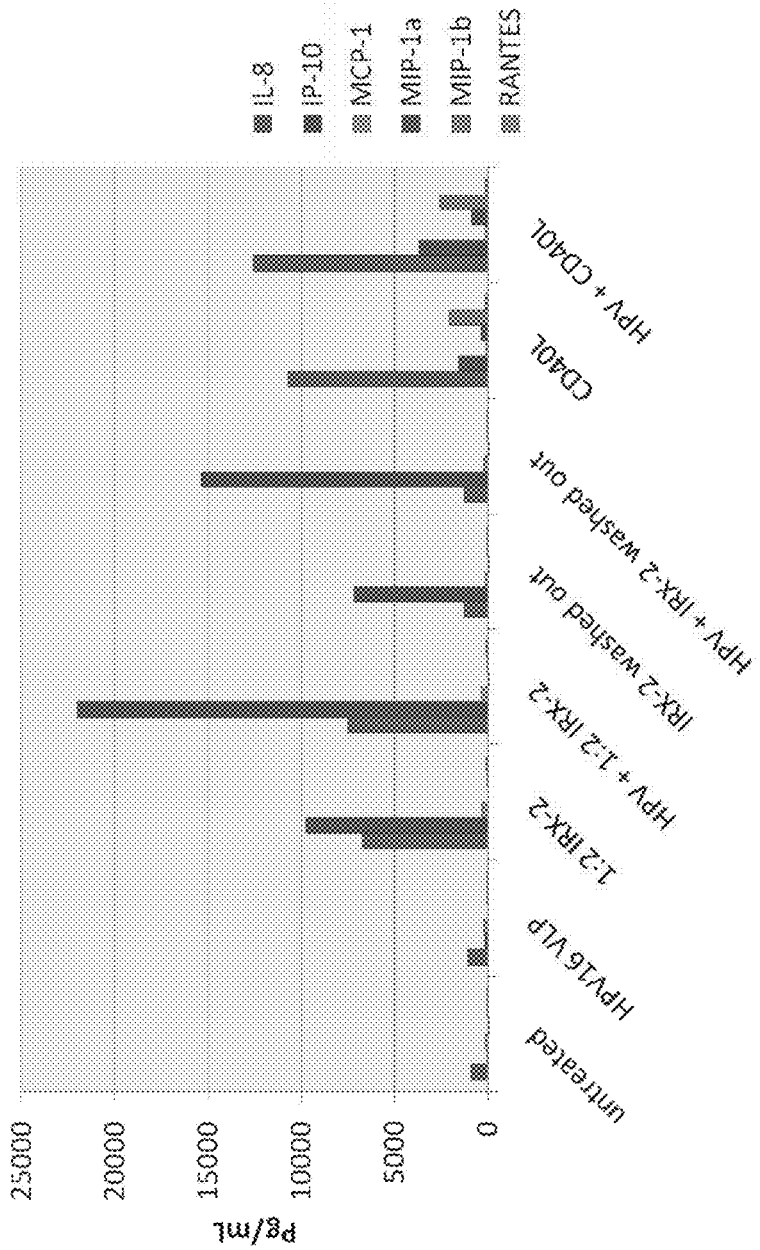
FIG. 9 is a graph showing human Langerhans cells treated with IRX-2 after HPV exposure secrete high levels of IL-8 and IP-10.

Treatment of LC with IRX-2 significantly increased the secretion of two Th1 associated chemokines, IP-10 and IP10 (FIG. 9). Both chemokines are pro-inflammatory, and IP-10 is known to attract T cells, NK cells, and monocytes to sites of inflammation. The results show that, under IRX-2 stimulation, L1 L2 VLP-exposed LC were gaining back their immunostimulatory capacity in the presence of HPV.

CONCLUSION

IRX-2 phenotypically and functionally activated human LC from healthy donors, even after they were exposed to HPV L1 L2 VLP. Increased levels of MHC and surface activation molecules, increased secretion of inflammatory and T cell activating cytokines and chemokines, and an increased ability to perform chemokine-directed migration after HPV and IRX-2 treatment (FIGS. 6-9), These results all support the effectiveness of the present invention in overcoming HPV-induced tolerization of LC and providing treatment for HPV infections. The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A method of immunotherapy for treating a viral infection caused by human papillomavirus (HPV) in a patient, comprising:

administering an effective amount of a primary cell-derived biologic to a patient having a viral infection caused by HPV in order to alleviate or eliminate the infection, such that an immune response is induced to the HPV in the patient which does alleviate or eliminate the infection, and wherein the primary cell-derived biologic comprises the cytokines interleukin (IL)-1, interleukin (IL)-2, interleukin (IL)-6, interleukin (IL)-8, interferon (IFN)-gamma and tumor necrosis factor (TNF)-alpha.

2. The method of claim 1, wherein the primary cell-derived biologic includes a concentration of IL-1 from 60-6,000 pcg/mL, a concentration of IL-2 from 600-60,000 pcg/mL, a concentration of IL-6 from 60-6,000 pcg/mL, a concentration of IL-8 from 6000-600,000 pcg/mL, a concentration of TNF-alpha from 200-20,000 pcg/mL, and a concentration of IFN-gamma from 200-20,000 pcg/mL.

3. The method of claim 1, wherein the primary cell-derived biologic further comprises interleukin (IL)-7, interleukin (IL)-12, interleukin (IL)-15, granulocyte-macrophage colony-stimulating factor (GM-CSF), and granulocyte colony-stimulating factor (G-CSF).

4. The method of claim 3, wherein the primary cell-derived biologic includes a concentration of IL-7 from 100-10,000 pcg/mL, a concentration of IL-12 from 100-10,000 pcg/mL, a concentration of IL-15 from 100-10,000 pcg/mL, a concentration of GM-CSF from 100-10,000 pcg/mL, and a concentration of G-CSF from 100-10,000 pcg/mL.

5. The method of claim 1, wherein the method further comprises:
administering an effective amount of one or more of a chemical inhibitor, a non-steroidal anti-inflammatory drug (NSAID), and zinc to the patient.

6. The method of claim 5, wherein the chemical inhibitor is cyclophosphamide.

7. The method of claim 5, wherein the NSAID is indomethacin.

8. The method of claim 1, wherein the primary cell-derived biologic is in a sterile, injectable solution.

9. The method of claim 1, wherein the administering of the primary cell-derived biologic is injection into the patient's epithelium.

10. The method of claim 1, wherein the administering of the primary cell-derived biologic is topical application to the patient's epithelium.

11. The method of claim 1, wherein administration of the primary cell-derived biologic prevents new HPV-induced lesions from developing.

12. The method of claim 1, wherein the patient has not received surgery, radiotherapy, chemotherapy, or combinations thereof, prior to administration of the primary cell-derived biologic.

13. The method of claim 1, wherein the patient is a man.

14. The method of claim 13, wherein the patient does not have cancer.

15. The method of claim 1, wherein the patient is a woman.

16. The method of claim 15, wherein the patient does not have cancer.

* * * * *